United States Patent
Karasahin

(10) Patent No.: US 11,723,788 B2
(45) Date of Patent: Aug. 15, 2023

(54) ADAPTIVE THREE-DIMENSIONAL ORTHOSES AND METHODS FOR THEIR MANUFACTURE AND USE

(71) Applicant: Osteoid Saglik Teknolojileri A.S., Istanbul (TR)

(72) Inventor: Deniz Karasahin, Izmir (TR)

(73) Assignee: Osteoid Saglik Teknolojileri A.S., Istanbul (TR)

(*) Notice: Subject to any disclaimer, the term of this patent is extended or adjusted under 35 U.S.C. 154(b) by 263 days.

(21) Appl. No.: 17/178,136

(22) Filed: Feb. 17, 2021

(65) Prior Publication Data
US 2021/0205115 A1    Jul. 8, 2021

Related U.S. Application Data

(60) Division of application No. 15/730,201, filed on Oct. 11, 2017, now Pat. No. 10,932,940, which is a (Continued)

(51) Int. Cl.
*A61F 5/05* (2006.01)
*A61F 5/02* (2006.01)
(Continued)

(52) U.S. Cl.
CPC ............ *A61F 5/05841* (2013.01); *A61F 5/01* (2013.01); *A61F 5/0102* (2013.01); *A61F 5/022* (2013.01);
(Continued)

(58) Field of Classification Search
CPC .......... B23P 11/00; A61F 5/0102; A61F 5/01; A61F 5/022; A61F 5/05841; A61F 2005/0167; A61F 2005/0197; G16H 50/50
See application file for complete search history.

(56) References Cited

U.S. PATENT DOCUMENTS 3,955,565 A * 5/1976 Johnson, Jr. ............ A61F 13/04
                                                        128/DIG. 20
4,905,681 A * 3/1990 Glascock .............. A61F 15/008
                                                                2/9
(Continued)

FOREIGN PATENT DOCUMENTS

EP    2671544 A2 *  9/2012    ............... A61F 5/01
EP    2671544 A2    12/2013
(Continued)

OTHER PUBLICATIONS

PCT/IB2016/000897 International Search Report dated Sep. 16, 2016.
(Continued)

*Primary Examiner* — Bayan Salone
(74) *Attorney, Agent, or Firm* — Wilson Sonsini Goodrich & Rosati

(57) ABSTRACT

A conformable body interface is fabricated using a data set representing a three-dimensional, soft tissue body surface. The conformable body interface includes a body scaffold that is divided into two or more longitudinal segments separated by axial joints. Optionally, the body scaffold is further divided into two or more circumferentially split segments separated by circumferential joints. The axial joints are circumferentially constrained by elastic bands, tabs, or similar structures and the circumferential joints are longitudinally constrained by elastic axial tethers or similar structures. In this way, the body interfaces can accommodate swelling and bending of the body surface.

3 Claims, 30 Drawing Sheets

Related U.S. Application Data continuation of application No. PCT/IB2016/000897, filed on Apr. 21, 2016.

(60) Provisional application No. 62/151,920, filed on Apr. 23, 2015.

(51) Int. Cl.
    *A61F 5/01* (2006.01)
    *B23P 11/00* (2006.01)
    *A61F 5/058* (2006.01)
    *G16H 50/50* (2018.01)

(52) U.S. Cl.
    CPC ....... *B23P 11/00* (2013.01); *A61F 2005/0167* (2013.01); *A61F 2005/0197* (2013.01); *G16H 50/50* (2018.01)

(56) References Cited

U.S. PATENT DOCUMENTS

| | | | |
|---|---|---|---|
| 5,107,854 A * | 4/1992 | Knotts | A61B 5/1036 600/592 |
| 5,571,206 A | 11/1996 | Varn | |
| 5,776,088 A | 7/1998 | Sereboff | |
| 5,823,975 A * | 10/1998 | Stark | A61B 5/1071 600/595 |
| 5,836,902 A * | 11/1998 | Gray | A61F 5/0111 602/5 |
| 6,058,503 A * | 5/2000 | Williams | A41D 13/08 2/24 |
| 6,179,800 B1 | 1/2001 | Torrens | |
| 6,725,118 B1 | 4/2004 | Fried et al. | |
| 6,840,916 B2 | 1/2005 | Kozersky | |
| 7,335,177 B2 | 2/2008 | Reynolds et al. | |
| 7,632,216 B2 | 12/2009 | Rahman et al. | |
| 7,981,068 B2 | 7/2011 | Thorgilsdottir et al. | |
| 8,002,724 B2 | 8/2011 | Hu et al. | |
| 8,613,716 B2 | 12/2013 | Summit et al. | |
| 10,932,940 B2 * | 3/2021 | Karasahin | B23P 11/00 |
| 2003/0032906 A1 | 2/2003 | Narula et al. | |
| 2005/0171461 A1 | 8/2005 | Pick | |
| 2006/0030802 A1 | 2/2006 | Nordt et al. | |
| 2007/0132722 A1 | 6/2007 | Kim et al. | |
| 2009/0146142 A1 | 6/2009 | Kim et al. | |
| 2011/0004074 A1 | 1/2011 | V'Arunraj et al. | |
| 2011/0301520 A1 | 12/2011 | Summit et al. | |
| 2011/0302694 A1 | 12/2011 | Wang et al. | |
| 2013/0150762 A1 * | 6/2013 | Summit | A61F 5/05841 602/20 |
| 2014/0012171 A1 | 1/2014 | Brown et al. | |
| 2015/0088046 A1 | 3/2015 | Walborn et al. | |
| 2015/0272764 A1 | 10/2015 | Kim et al. | |

FOREIGN PATENT DOCUMENTS

| | | | | |
|---|---|---|---|---|
| EP | 3285647 B1 * | 9/2019 | | A61F 5/01 |
| WO | WO-2016071773 A2 | 5/2016 | | |
| WO | WO-2016170433 A1 * | 10/2016 | | A61F 5/01 |

OTHER PUBLICATIONS

Office action dated Mar. 10, 2020 for U.S. Appl. No. 15/730,201.
U.S. Appl. No. 15/730,201 Notice of Allowance dated Nov. 5, 2020.

* cited by examiner

ADAPTIVE THREE-DIMENSIONAL ORTHOSES AND METHODS FOR THEIR MANUFACTURE AND USE

CROSS-REFERENCE TO RELATED APPLICATION

The present application is a divisional of U.S. patent application Ser. No. 15/730,201, filed Oct. 11, 2017, which is a continuation of PCT Application No. PCT/IB2016/000897, filed Apr. 21, 2016, which claims the benefit of Provisional No. 62/151,920, filed on Apr. 23, 2015, the entire content of which are incorporated herein by reference.

BACKGROUND OF THE INVENTION

1. Field of the Invention

While orthotic intervention for physical rehabilitation has been known for centuries, splints, casts, and other orthoses still present challenges in implementation. Starting with temporary immobilization using splints made from sticks and casts made from plaster, the field has progressed to fabricating dynamic orthoses from advanced composites. Recently, the field has progressed to the production of three-dimensional orthoses individualized for patient anatomies using three-dimensional scanning and printing techniques.

The primary functions of any cast or splint are to provide an external structure and to create physical conditions which promote healing with minimal complication. Traditional casts and splits often fail in at least one of these functions.

Swelling (compartment pressure development) must be taken in to consideration during casting of a splint. In standard procedures, the medical professional preparing a conventional hard-shell cast leaves significant space for swelling of the injured anatomy. If made too tightly, the cast will restrict circulation, cause pain discomfort, and may lead to compartment syndrome. If made too loosely, the will fail to provide a stable environment for the healing process. Often, patients are provided initially with a cast large enough to accommodate expected swelling, and later with a relatively tighter cast to more closely conform to the anatomy. The need to change cast or splints is of course inconvenient.

Atrophy is another common problem associated with long-term cast usage. Atrophy is the wasting or loss of muscle tissue due to lack of physical activity caused by the splint's immobilization. Decreases in muscle size, strength and mobility are often observed. Loss in muscle size will often prevent the splint from providing the support and stability needed to promote the healing process and may cause delayed union, non-union and mal-union of the fracture.

Joint stiffness can be another problem associated with long-term splint or cast usage. Joint stiffness is the loss or reduction in range of motion in a joint caused resulting from long-term joint immobilization. Joint stiffness may be lessened or prevented by utilizing a dynamic or an adjustable passive orthotic product which allowing some joint motion during the orthotic intervention.

External pressure may be applied to a fractured bone to promote healing. By applying external pressure during hardening, a cast or other orthosis will often be able to apply a greater pressure on the bone during the subsequent healing period. Such external pressure can reduce the occurrence of complications such as delayed union, mal-union, and non-union of the fracture.

For these reasons, it would be desirable to provide improved designs and methods for fabricating splints, casts, and other orthoses. The designs should allow for orthoses that can accommodate swelling after the orthosis has been fitted on a patient, should allow for a controlled application of pressure to the anatomy to promote bone growth during healing, should allow for individualizing an orthosis for specific patients, and should achieve these objectives in an efficient and cost effective manner. At least some of these objectives will be achieved by the inventions described hereinbelow.

2. Description of the Background Art

Casts, boots, and other shells which circumscribe a body limb or other anatomy and which are axially spilt to allow for expansion and/or removal are described in U.S. Patent Publication Nos. 2015/0272764; 2015/0088046; 2014/0012171; 2013/0150762; and 2005/0171461; and U.S. Pat. Nos. 8,002,724; 5,776,088; 5,571,206; 7,981,068; 7,335,177; 6,840,916; and 3,955,565. Other relevant background patents and publications include U.S. Pat. Nos. 5,107,854; 5,823,975; 5,836,902; 6,179,800; 6,725,118; 7,632,216; 8,613,716; and U.S. Publication Nos. 2003/0032906; 2007/0132722; 2009/146142; 2011/0004074; 2011/0301520; 2011/0302694; and European Patent No. 2671544.

BRIEF SUMMARY OF THE INVENTION

The present invention utilizes computer-aided design, software analytics, digital manufacturing, sensing, digital data collection, and analytical technologies to create a digital process for manufacturing, full-contact exo-skeletal orthoses with adaptable and/or adjustable structural elements. Such orthoses are capable of providing a controlled, medically beneficial interface with a patient body surface or other patient anatomy in order to reduce complications, promote better healing, and enhance protection of the anatomy being treated. The present invention provides orthoses, such as splints and casts, having body scaffolds that are axially and/or radially split into a plurality of segments or cells separated by joints that allow expansion in response to swelling. The segments or cells are assembled with elastic mechanical restraints that hold the segments and cells together and further apply external pressure when a covered body surface undergoes swelling. The present invention provides a swelling management system (SMS), a stiffness prevention system (SPS), methods for applying external pressure through the orthotic and modular components. In addition to providing direct medical intervention through the structural and modular components of the orthotic, the present invention can further provide locations for interfacing sensors with the body surface. The sensors in turn can provide data for real-time patient monitoring and for subsequent data mining.

The SMS introduces semi-dynamic self-aligning structure(s) and components (mechanisms) to enable reducing or increasing the cross-sectional diameter and/or area of a body scaffold in response to post-trauma swelling followed by atrophy (decrease in the size of muscles), while maintaining the body scaffold's ability to provide a full contact hard shell orthosis.

SPS is a supplement to SMS to enable limited mobility on desired joints in desired axis of motion (flexion, extension, abduction, adduction, pronation, and supination) through splint topology modifications and/or introduction of additional mechanical components.

The invention also incorporates methods for applying external pressure through adjustable modular units positioned on a body scaffold and methods for monitoring the applied pressure.

The invention also incorporates methods for delivering therapeutic stimulation through modular units positioned on a body scaffold.

Exemplary applications for the three-dimensional orthose of the present inventions include upper-limb orthoses, lower-limb orthoses, spinal and neck orthoses, wrist orthoses, ankle orthoses, and similar applications.

The present invention relies on known three-dimensional printing techniques for manufacturing personalized body scaffold. The methods may generally include three steps. First, known three-dimensional scanning or imaging technologies are used to directly or indirectly (from a mold) to generate a three-dimension data set representing a target body surface geometry. This three-dimensional data set will typically represent an interior geometry of the body scaffold being produced. Second, a physical structure for the custom three-dimensionally printed body scaffold is determined and modeling. During the determining and modeling step, specific design features of the body scaffold, such as large window openings or any three-dimensional modification applicable to body scaffolds or conventional orthotics can be marked on a patient's skin with ink markers. A CAD designer can reference the markings and follow them as instructions as the design file is being created. The CAD designer may employ know design software and may follow any one or more of a variety of design protocols, such as finite element analysis, generative design, parametric design, and virtual and augmented reality technologies. Third, three-dimensional printing or other digital or numerically controlled fabrication methods produce the personalized body scaffold. The scaffolds may also be designed to incorporate other capabilities including internet-of-things (TOT) devices and systems, signal processing units, wireless communication units (Bluetooth®, infrared, GSM, local wireless networks, and internet connectivity), on-board or remote interfaces (tactile, photometric, augmented or virtual reality interface, web or software interface linked mobile devices, smart phones, LED, LCD, tablets, laptops etc.), various types of power sources (including thermoelectric generation, wireless energy transfer technologies, alternative and direct current), cloud computing and storage units.

Although the invention has been described as an adjustable, typically self-adjustable, body scaffold with a plurality of self-aligning surfaces and elements for humans, in other embodiments is possible to adopt other products used by humans including, chairs, seats, saddles, athletic equipment, shoes, padding, helmets and partial or full body exoskeletal suits, etc. The embodiments of the invention can also be used for casts/braces for animals and custom saddles for horses and equestrians.

In a first aspect, the present invention provides a conformable body interface which may be in the form of a splint, a cast, or other structure intended to at least partially surround and support some portion of the patient's anatomy, particularly including body limbs, body joints, a portion of the torso, and the like. Most commonly, the conformable body interface will be in the form of an orthotic intended to support a body limb or body joint, typically after a fracture or other injury to the limb or joint.

The conformable body interfaces comprises a body scaffold, typically formed as a three-dimensional lattice, which has a longitudinal axis which will typically be aligned with a dimension of the patient's anatomy, for example, being aligned with or along length of a bone in the arm, leg, or body joint. The body scaffold is typically configured to be removably placed over a conforming body surface, and the body scaffold will be divided into two or more longitudinal segments separated by axial joints. The axial joints, in turn, are configured to circumferentially separate which allows circumferential expansion of the scaffold in response to swelling of the body surface that often occurs during the healing process. The conformable body interface will usually further include a plurality of elastic constraints that span the axial joints at axially spaced-apart locations along the body scaffold. The constraints are configured to elastically constrain radial expansion of the body scaffold so that the scaffold can accommodate swelling of the body surface while maintaining a desired inward or supportive pressure against the body surface.

An exemplary embodiment, the body scaffold comprises a three-dimensional lattice which may be produced by three-dimensional printing or similar digitally controlled production techniques, such as stereo lithography (SLA), numerically controlled machining, and the like. The lattice will have gaps, spaces, apertures, and the like, and such open structures are suitable for a number of purposes, including placement of sensors for engagement against the body surface, such as described in co-pending international patent application number PCT/IB 2015/002432, the full disclosure of which is incorporated herein by reference.

In further exemplary embodiments, the elastic constraints that span the axial joints may comprise any one of a variety of structures which fully or partially circumscribe the body scaffold. For example, the elastic constraints may comprise elastic bands that fully circumscribe the body scaffold. Such elastic bands may be continuously elastic over their lengths, often having a uniform elasticity at all points along their lengths. Alternatively, the elastic bands may have discontinuous elasticity over their lengths. For example, the elastic bands may have elastic portions separated by inelastic or non-distensible portions. The elastic portions can be formed from elastic polymers, mechanical springs, or the like, while the inelastic portions could be formed from non-elastic polymers and other non-distensible structures and materials.

In alternative embodiments, the elastic constraints may comprise elastic tabs having ends which are attached to the longitudinal segments and which do not fully circumscribe the body scaffold. Typically, such tabs will have one end attached to a first longitudinal segment and a second end which is detachably or non-detachably attached to an adjacent longitudinal segment. In other embodiments, such tabs may span more than two adjacent longitudinal segments while being detachably or non-detachably secured to any two or more of those segments. When the elastic constraints comprise elastic tabs, the elastic tabs may be circumferentially aligned around the body scaffold so that they form a generally continuous line of elasticity around that circumference. Alternatively, elastic tabs may be actually offset from each other at any pattern which is selected to provide specific elastic characteristics on the body scaffold at particular anatomical locations. By using elastic tabs which are detachably secured at least one end, the tabs may be detached in order to facilitate donning and removal of the conformable body interface over the body surface.

The elastic constraints will typically have fixed lengths, particularly when they're formed as a continuous band structure. Alternatively, in some cases, elastic bands may have adjustable lengths, e.g. allowing the bands to be cinched and/or loosened after placement over the body scaffold. Similarly, when tabs are employed as the elastic bands, the tabs may have fixed or adjustable lengths. In still further embodiments, the elastic constraints may provide other functionalities, for example including stress/strain transducers that allow measurement of force resulting from radial expansion of the body scaffold, allowing monitoring of body swelling during treatment.

In still further alternate embodiments, in addition to or instead of the plurality of discrete elastic constraints, one or more fully or partially elastic covers, such as mesh or fabric sleeves, may be placed over the body scaffold to provide or contribute to the radially inward force on the body scaffold.

In exemplary embodiments, the actual joints comprise slip joints, typically comprising a male element along an edge of one longitudinal segment and a female element along the edge of the adjacent longitudinal segment. Such slip joints allow expansion and contraction of joints while maintaining alignment of the adjacent longitudinal segments. In some cases, mechanisms can be provided for locking or adjusting the opening of the slip joints to prevent or control such lateral translation. Such locking mechanism may comprise various elements, such as pins, pawls, gears, and the like. Pins may be used to lock the slip joints by dropping them into holes aligned in the slip joints to immobilize the joints at prescribed spaced-apart dimensions. Gears and pawls, in contrast, may be used to actively adjust and control the spacing between adjacent longitudinal segments.

Usually, the body scaffold is further divided into two or more circumferentially split segments separated by circumferential joints. The circumferential joints are configured to axially separate in response to movement of the body surface, for example bending of a body joint. The two or more circumferentially split segments are typically held together by a plurality of elastic axial tethers, where the tethers typically pass through axial channels formed in or through the circumferentially split segments. The axial tethers will usually be anchored at one end at or near a distal circumferentially split segment and at another end in a proximal circumferentially split segment. The circumferential joints are also typically slip joints that will allow pivoting between adjacent circumferentially split segments.

In a second aspect, the present invention provides methods for fabricating conformable body interfaces, such as those described above. Such fabrication methods comprise obtaining a data set representing a three-dimensional soft tissue body surface, which may be any of the tissue surfaces described above. A three-dimensional body scaffold is fabricated based on the data set so that the scaffold can be removably placed over the three-dimensional body surface to conform to at least some target regions on the surface. In particular, the data set defines a body scaffold that is divided into two or more longitudinal segments having axial joints therebetween. The axial joints are configured to separate in response to swelling of the body surface when the scaffold is placed over the body surface, typically during healing of an injury.

In preferred aspects of the method, the data set further defines features on the body scaffold configured to receive a plurality of elastic constraints spanning the axial joints at axially spaced-apart location along the body scaffold. Such elastic constraints are able to elastically constrain radial expansion of the body scaffold in response to swelling of the body surface. The data set typically further defines two or more circumferentially split segments separated by circumferential joints, which are configured to axially separate in response to movement of the body surface when the scaffold is placed over the body's surface during patient healing. In such cases, the data set typically still further defines axial channels on the body scaffold. The channels are located and configured to receive a plurality of elastic axial tethers spanning the circumferential joints at circumferentially spaced-apart locations on the body scaffold to elastically constraining bending of the body scaffold. These fabrication methods are typically performed using known three-dimensional printing and fabrication methods, such as three-dimension printing, stereo lithography (SLA), and the use of numerically controlled machines for machining the body components. After the discrete components of the body scaffold are fabricated, the body scaffold may be further fabricated by attaching elastic and/or non-elastic constraints to the features formed on the longitudinal segments and positioning axial tethers within the axial channels that span the circumferential joints between adjacent circumferential segments.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The present invention provides a custom designed full contact exo-skeletal cast/splint with a plurality of adjustable and/or self-adjusting structural components closely fitted to a portion of human anatomy. The structural solutions of the invention are developed in order to promote a controlled and medically beneficial relationship between the orthotic and the patient. Although the structural solutions of the invention are particularly suitable for post-fracture applications, the methods and techniques described herein may also be used to treat other musculoskeletal and neuromuscular conditions requiring periods of orthotic intervention. The apparatus and methods of the present invention address a series of very commonly observed complications in post fracture management.

Figure 1:
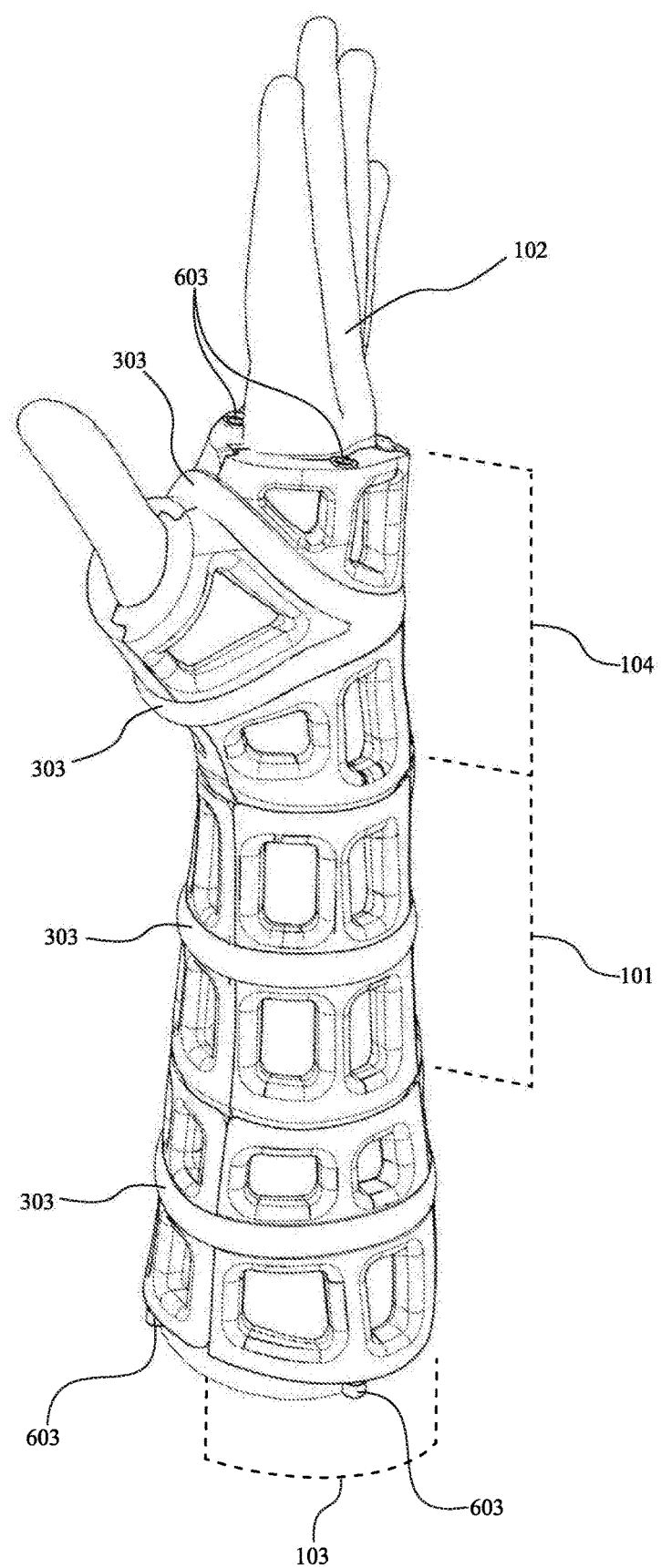
FIG. 1 is an embodiment of an adaptive splint with four longitudinally split segments and three circumferentially split segments, comprising of a total of twelve individual body scaffold cells held together with three elastic radial restraints and four axial tethers.
Figure 2:
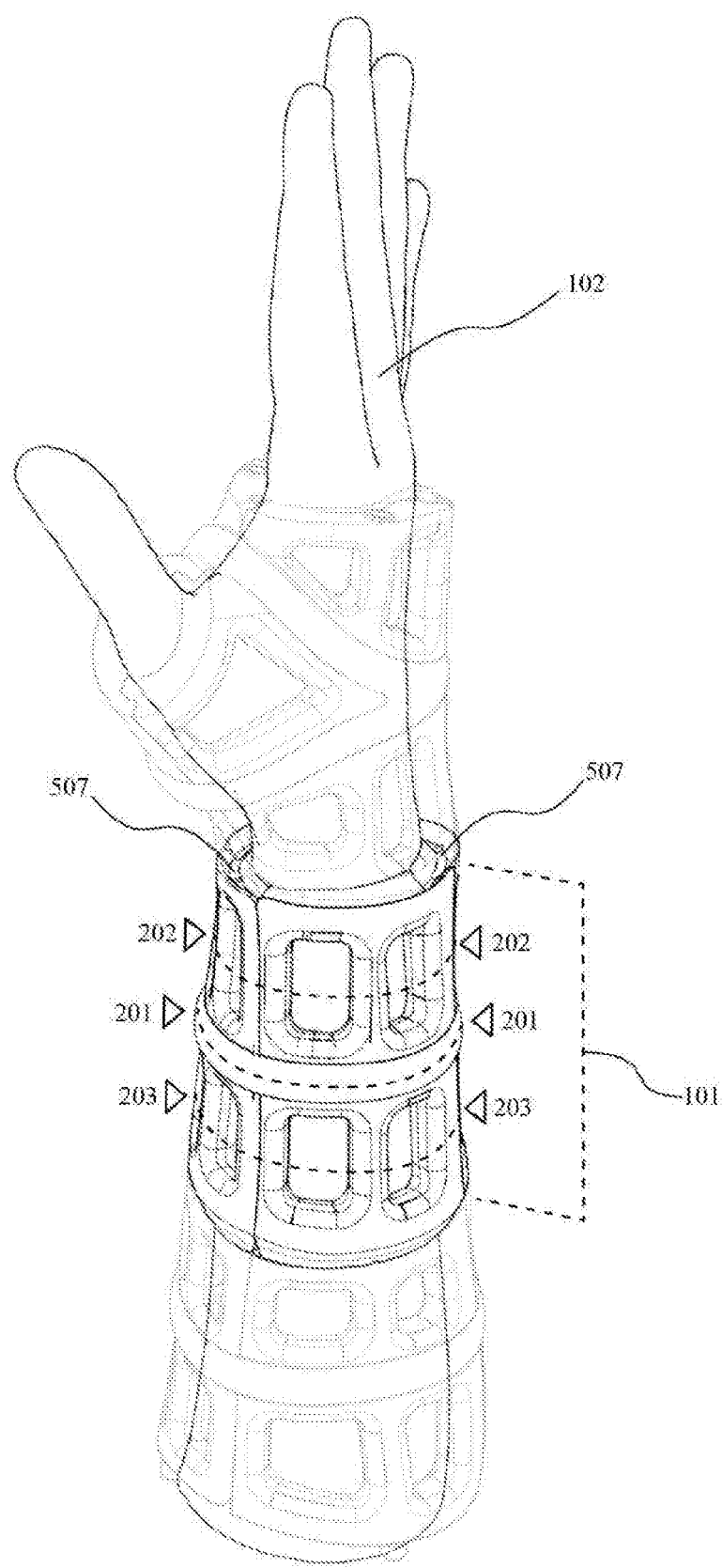
FIG. 2 is a circumferential portion of a personalized splint or other body scaffold with four longitudinally split segments.
Figure 3:
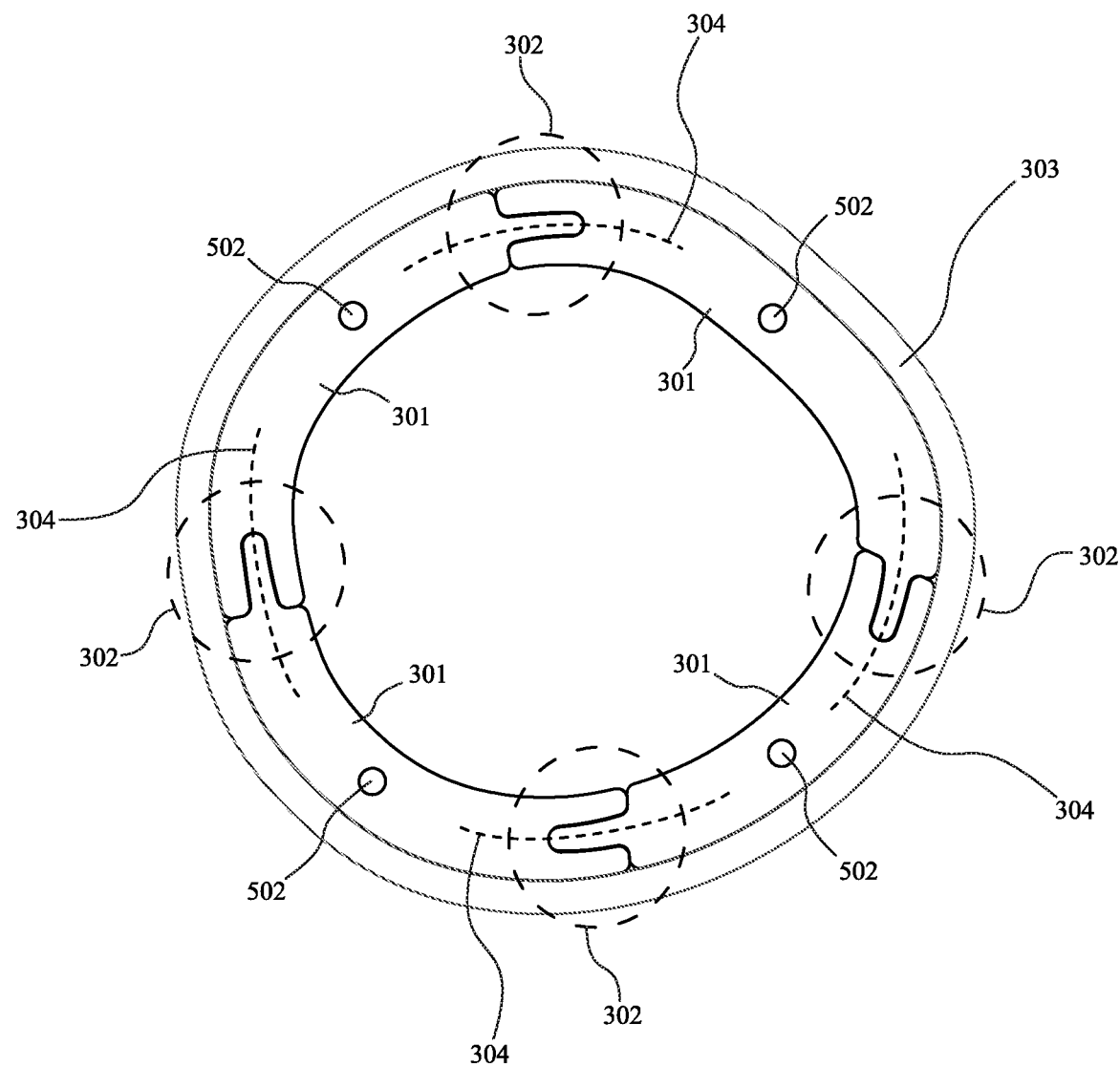
FIG. 3 is a transverse cross-section of the splint of FIG. 2 shown without radial expansion.
Figure 4:
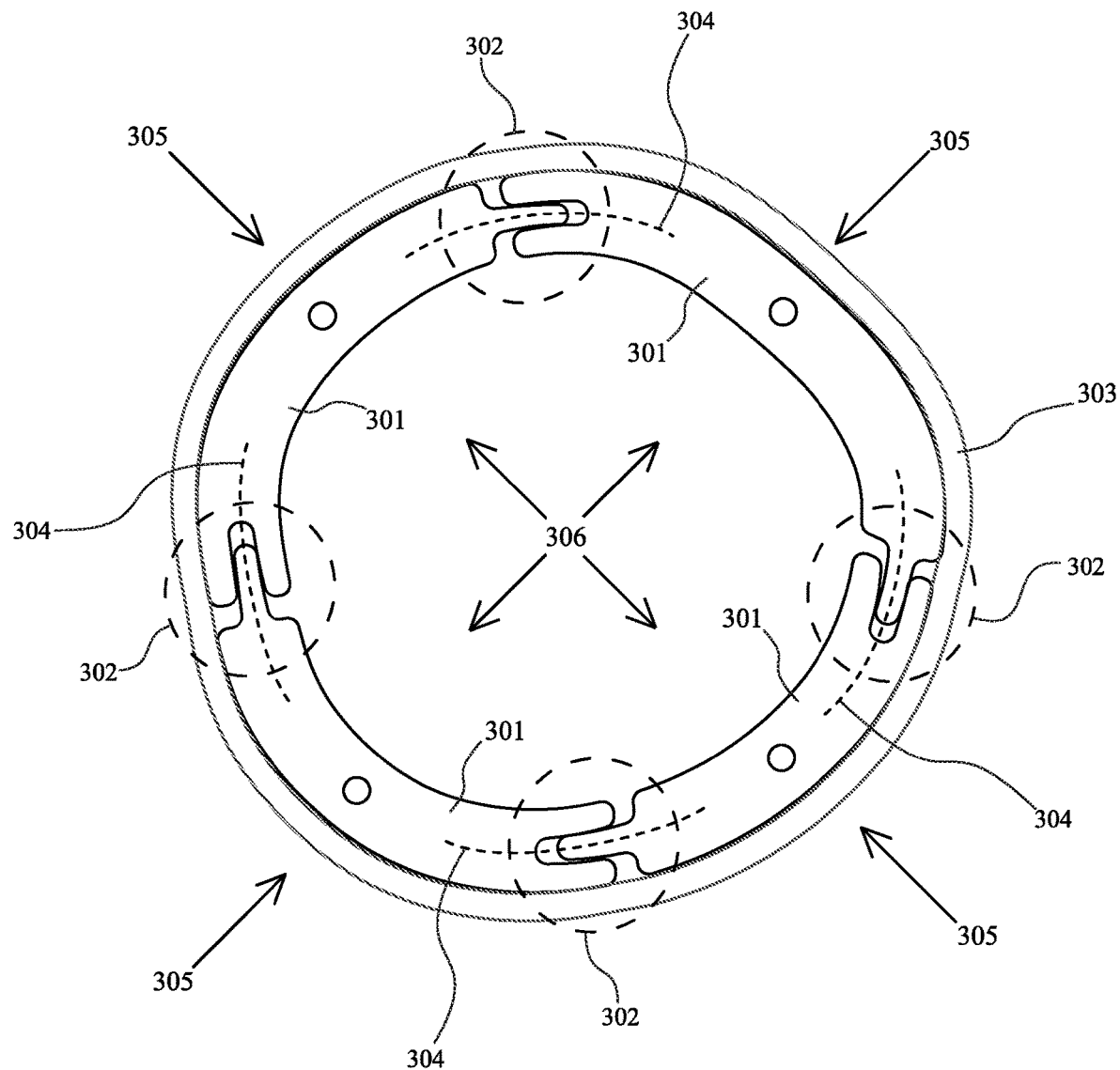
FIG. 4 is similar to FIG. 3 shown with radial expansion.

A Swelling Management System (SMS) introduces circumferential adjustment capabilities (increase or decrease) to personalized body scaffolds in order to accommodate swelling and atrophy during an immobilization period. SMS is implemented through dividing a portion (or portions) of a body scaffold along longitudinal lines into a plurality of segments (two, three, four or more) in order to create the basis for a semi-dynamic structure. The axially divided segments (referred to as "longitudinal segments") interface at "circumferential joints" between neighboring longitudinal segments. An "elastic constraint" circumferentially restrains the separable longitudinal segments, typically an elastic band or other component or positioned around of in some cases embedded in the segmented body scaffold. An exemplary body scaffold structure is illustrated in FIGS. 1-4 with four longitudinal segments 301 corresponding to a circumferential portion 101 of an upper extremity splint. FIGS. 3 and 4 show cross-sections taken through section 201 of FIG. 2.

Figure 27:
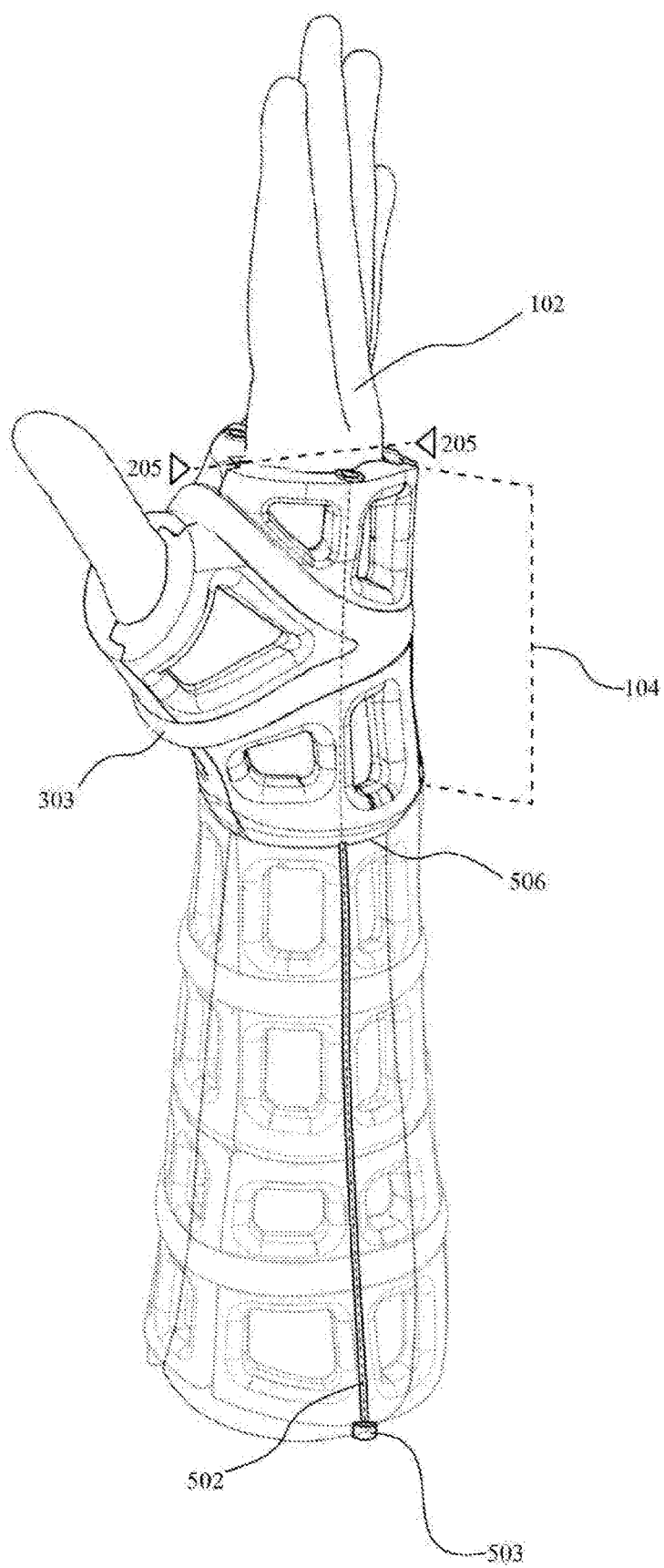
FIG. 27 illustrates an upper circumferential portion of a body scaffold with SMS.

A plurality of longitudinal segments 301 (also referred to as cells) together form a circumferential structure is illustrated in FIG. 3. The longitudinal segments 301 are joined by axial slip joints 302 that are located along the axial edges of each adjacent segment 301. The axial slip joints 302 allow the body scaffold to circumferentially expand over expansion paths 304 and also provide a physical limit for circumferential contraction. When fully contracted, the slip joints will be in a "negative locked state." When the axial slip joints are in a negative locked state, as illustrated in FIG. 3 (also in FIG. 5), the scaffold will protect the patient anatomy 102 from pressure and impact. The individual longitudinal segments 301 of the circumferential structure of the body scaffold are held together by one or more radial elastic constraining elements 303 that apply a radially inward constraining force on the longitudinal segments 301. The elastic constraint 303, may take the form of an O-ring or other structures with similar elastic properties (springs, etc.). Rather than using a single elastic restraining element, the same effect can be achieved using a plurality of elastic restraining and/or using non-circular elastic restraining elements such as elastic restraining element 303 in FIG. 27. FIG. 4 illustrates physical forces observed in section 201 in an event of circumferential expansion (an unlocked state) of axial slip joints 302, being relatively spaced-apart from each other. Arrows 305 illustrates the inward force generated by the elastic restraining structure 303. Arrows 306 illustrates the radially outward force generated by patient anatomy. As shown in FIG. 4 individual longitudinal segments 301 move circumferentially away from each other to accommodate swelling or other expansion of a patient anatomy. The axial slip joints 302 allow the necessary circumferential expansion following paths 304 between the cells. In this particular illustration, the dynamic structure (SMS) is in a state of equilibrium with patient anatomy providing an outward force that is balance by the inward force(s) of the elastic constraints 302. In FIG. 3, the system is in a negative locked state where the scaffold protects the anatomy from external pressure or impact.

The axial slip joints 302 can be configured to allow circumferential expansion and/or contraction of the body scaffold in response to swelling and/or atrophy that often occurs during the healing process. The dynamics of the system are illustrated in greater detail in FIGS. 5, 6 and 7 with focus to male edge 307 and female edge 308 of adjacent longitudinal segments (cells) 301 on their motion paths 304.

Figure 5:
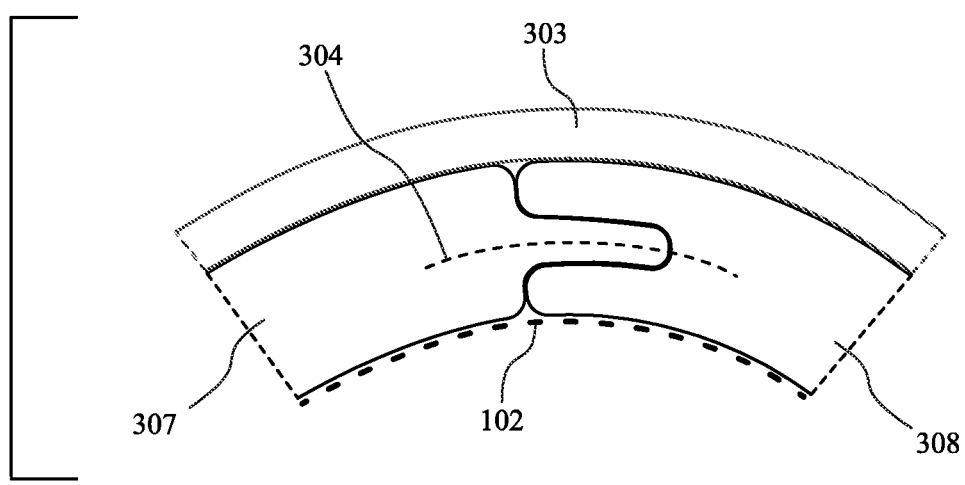
FIG. 5 is a transverse cross-section of a radial slip joint in a closed configuration.
Figure 6:
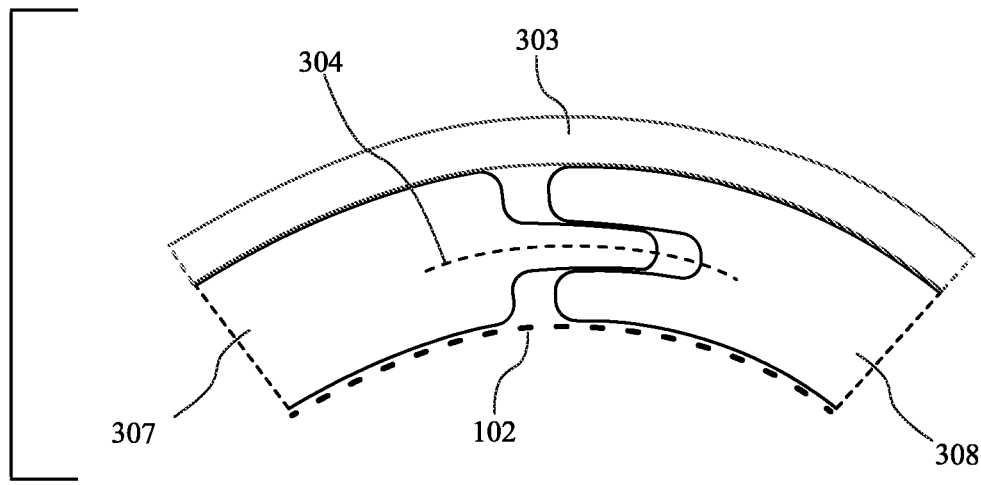
FIG. 6 is similar to FIG. 5 shown with the radial slip joint partially opened.
Figure 7:
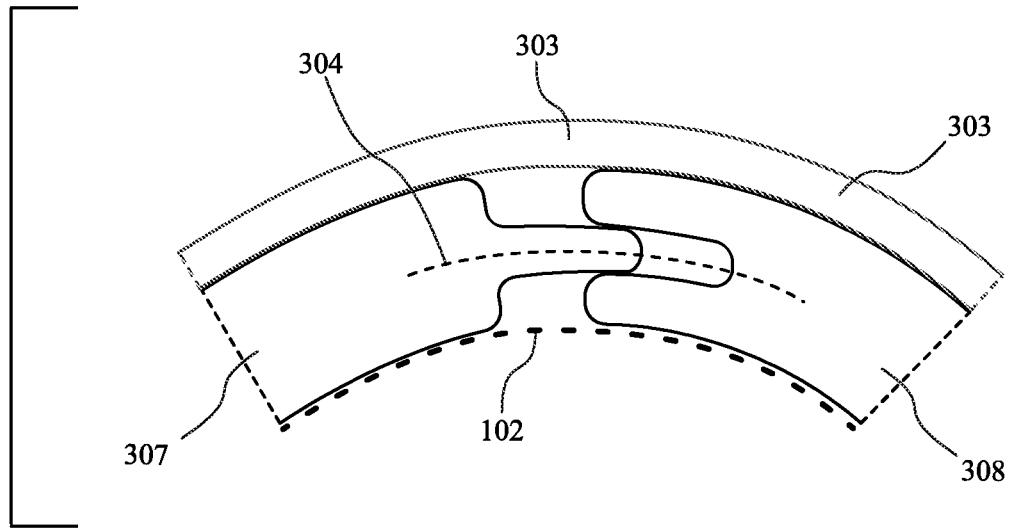
FIG. 7 is similar to FIG. 5 shown with the radial slip joint opened to a limit of circumferential expansion.

As shown in FIGS. 5, 6 and 7, the axial slip joints 302 can be configured to allow dynamic circumferential expansion of a portion (or portions) of a body scaffold in response to developing edema. The body scaffold is initially applied to the patient anatomy with the slip joints in their negative locked states as shown in FIG. 5. As edema develops, the male edge 307 and female edge 308 separate along path 304, as shown in FIG. 6. FIG. 7 represents the structural limit of circumferential expansion. This limit, of course, can be extended by lengthening the male and female edge components. Circumferential expansion occurs only so long as the radially outward pressure generated by the patient anatomy 102 is greater than the radially inward pressure generated by the radial elastic restraining structure 303.

The axial slip joints 302 can also be configured to allow dynamic circumferential contraction of a portion (or portions) of a body scaffold in order to provide and maintain close contact and support to the patient anatomy during atrophy. The body scaffold is initially applied to the patient anatomy with the slip joint in their expanded states, as shown in FIG. 6 or 7. As the anatomy atrophies, the male and 307 and female edge 308 come together along path 304, being limited only by the negative locked state of FIG. 5. Circumferential contraction occurs only so long as the radially inward pressure generated by the radial elastic restraining structure 303 is greater than the radially outward pressure generated by the patient anatomy 102.

In another embodiment, the axial slip joints 302 can be configured to allow dynamic circumferential expansion and contraction of a portion (or portions) of a body scaffold in order to cope with developing edema fallowed by atrophy. For this particular application circumferentially apart axial slip joint topology is applied to the patient as illustrated in FIG. 6. As edema develops, components 307 and 308 re-arrange their positions with respect to motion path 304. FIG. 7 is a representation of re-arranged longitudinal segments with respect to increased muscle size, later on as edema disappear and give way to atrophy components 307 and 308 rearrange their position as represented in FIG. 5 in to a locked structural state.

Figure 8:
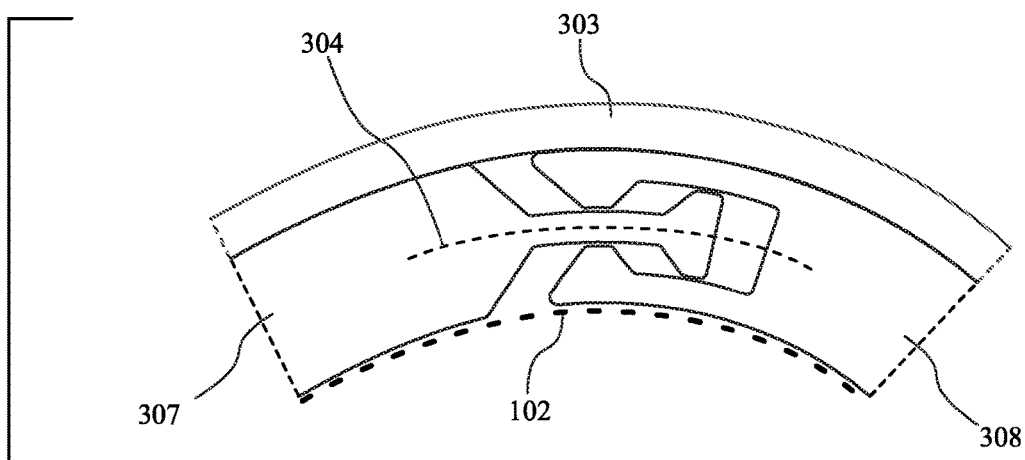
FIGS. 8-10 illustrate alternative radial slip joint configurations with stop elements that limit circumferential expansion.
Figure 9:
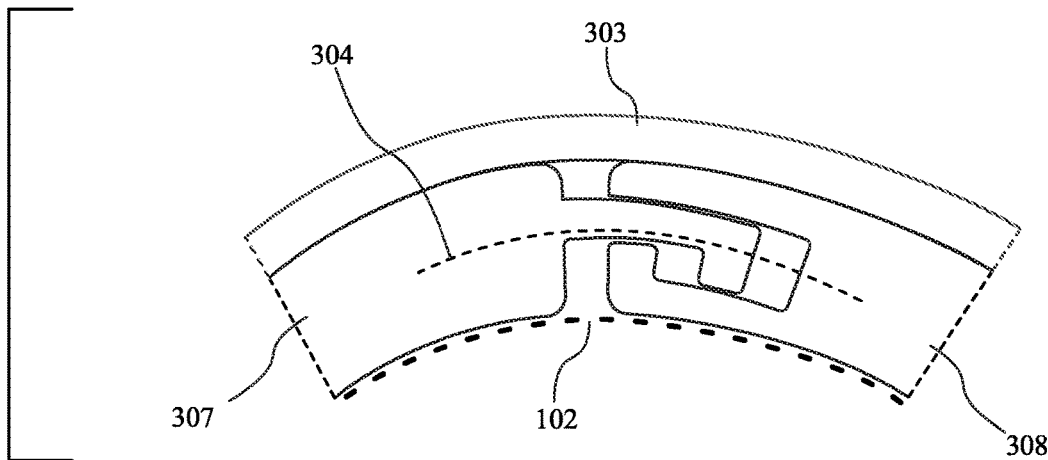
Figure 10:
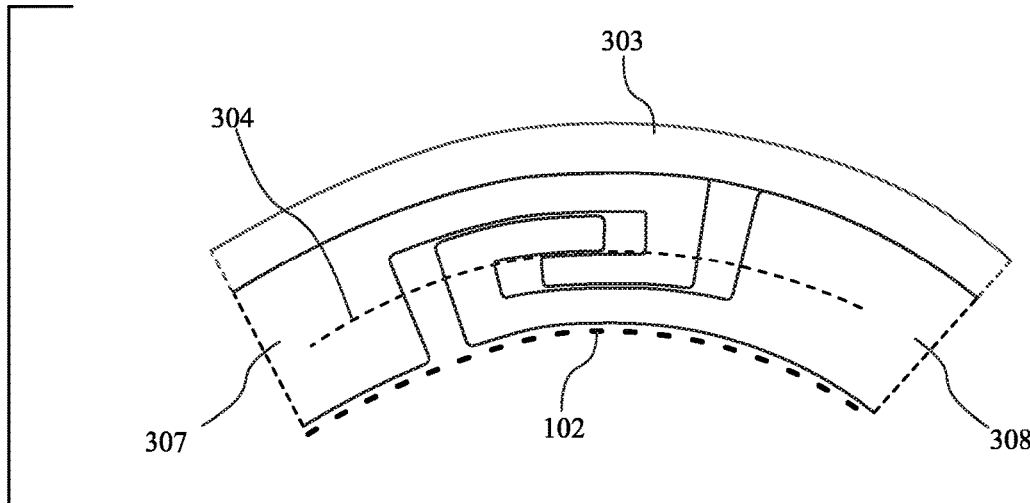

In another embodiment, alternative axial slip joint topologies, with relatively more complicated designs, are offering a positive locked state to SMS. A positive locked state, meaning having an additional physical limitation for circumferential expansion are illustrated in FIGS. 8, 9 and 10. Similar solutions corresponding one male end 307 and a fitting female end 308 of adjacent longitudinal segments with related motion paths 304 and the patient anatomy 102 are illustrated. In its essence, any topology providing any path (circular, non-circular, twisting, rotational, linear, non-linear, 3 dimensional) of motion between two or more adjacent segments with physical restraints is convenient for having a controlled and medically beneficial physical relationship with patient anatomy.

Circumferential pressure 305 is generated from radial elastic constraining element(s) 303 may either turn out to be beneficial or unbeneficial to the patient, depending on the nature and the state of the injury. Although SMS described above, create functioning structures with circumferential adjustment capabilities (increase or decrease), any pressure or impact can reach patient anatomy unless the system is in a negative locked state. FIGS. 11-17 demonstrate methods for locking or adjusting the opening of the slip joints to prevent or control such lateral translation. Additional locking mechanisms may need to be applied from one or more designated locations between male 307 and female 308 components of axial slip joints. For practical reasons (accessibility and ease of use), it may be beneficial but not essential to avoid radial elastic constraint element(s) 303. In a typical embodiment as illustrated in FIG. 2, convenient locations for adopting additional locking mechanisms are marked with sections 202 and 203.

Figure 11:
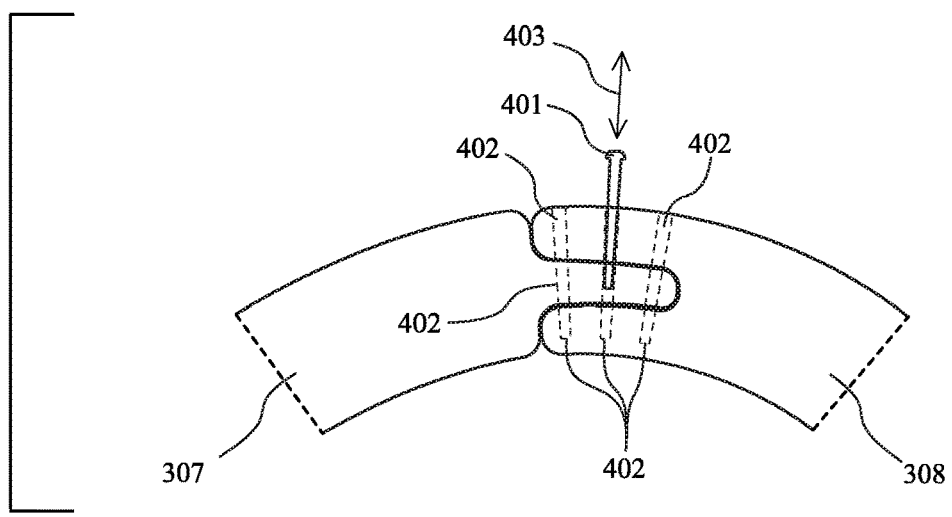
FIGS. 11-13 illustrate the radial slip joints of FIGS. 3-5 a locking mechanism having a locking pin for selectively preventing expansion and contraction of the joint at different degrees of opening.
Figure 12:
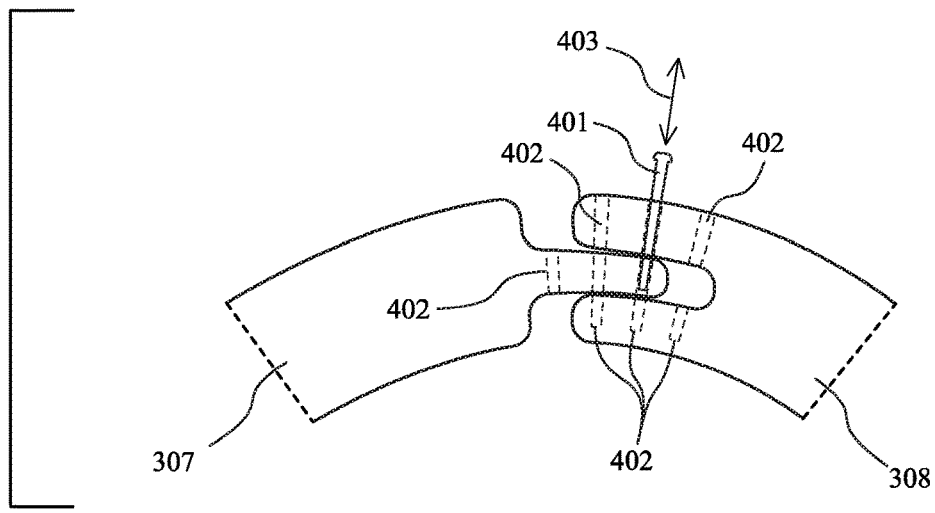
Figure 13:
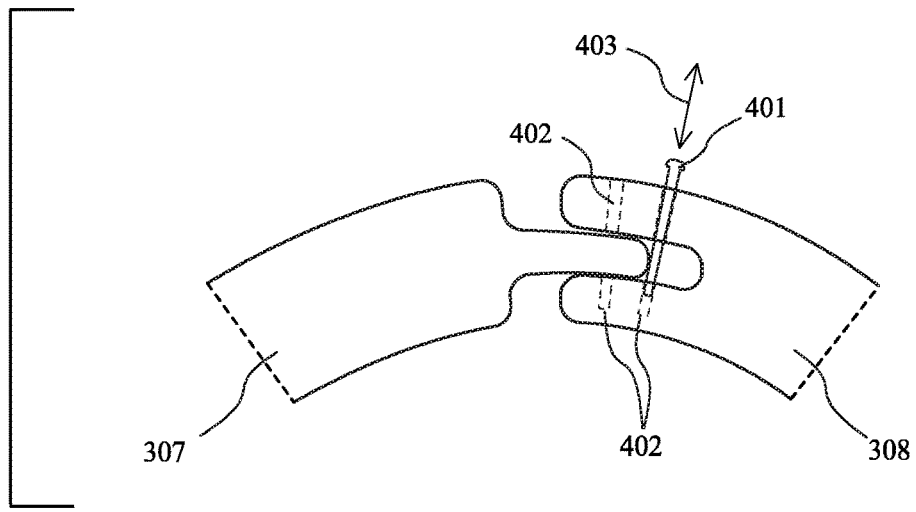

In one embodiment, an improved locking mechanism has locked and/or unlocked states, as illustrated in FIGS. 11-13. An exemplary locking mechanism comprises pin(s) 401 or similar restraining elements and fitting holes 402 aligned in axial slip joints. Pins 401 are used to block and adjust motion potential between segments by insertion or removal 403 into holes at prescribed spaced-apart locations. FIGS. 11 and 12 illustrate a method to create a completely fixed state between two adjacent segments. Self-arrangement potential between two individual cells for both circumferential increase and decrease can be temporarily disabled by fixing male 307 and female 308 cells by inserting a pin or similar restraining structures 401 through both of the elements. For this particular application suitable fitting hole geometries 402 must be presented on both male and female cells. A number of hole geometries can also be adapted to increase control over the fixed state between two cells. FIG. 13 illustrates a method to determine multiple positions to negative locked state and still allow circumferential increase. In greater detail, a geometric position of negative locked state between two individual cells can be arranged by inserting a pin or similar restraining structures 401 through female 308 element of a radial slip joint 302 and physically limit circumferential decrease and therefore the negative locked state of the system. Multiple hole geometries on female cells located on motion path can be adapted as well as sliding pins embedded in to slots in order to increase control over the negative locked state.

Figure 14:
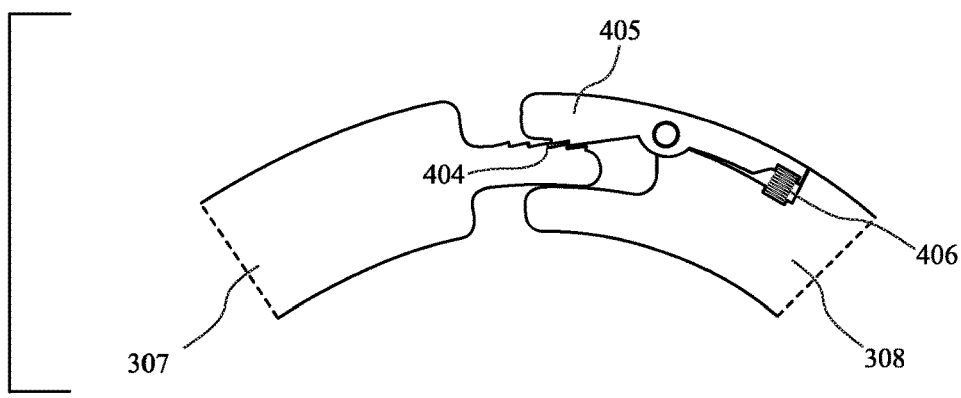
FIGS. 14-17 radial slip joints similar to those of FIGS. 3-5 having adjustable locking mechanisms with ratchet mechanisms and rack-and-pinion mechanism, for providing a plurality of negative locked states.
Figure 15:
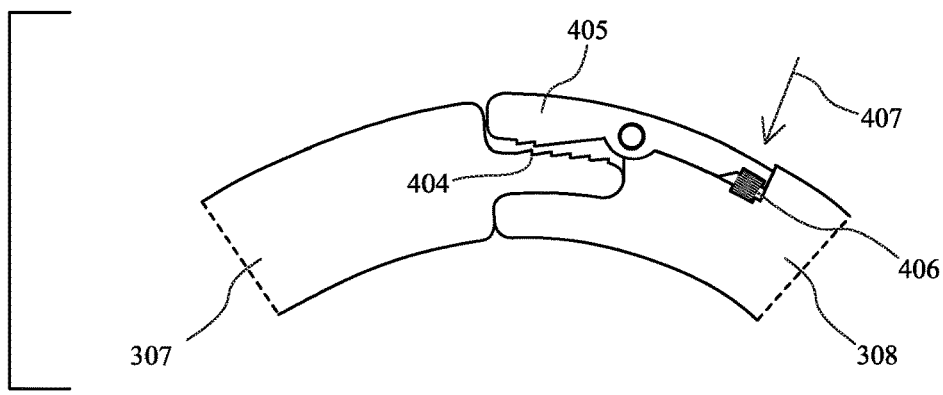

In another embodiment, an improved locking mechanism with multiple negative locked states is illustrated in FIGS. 14 and 15. The improvement involve the adaptation of a linear ratchet mechanism in order to allow continuous one directional special adjustment (circumferential increase for this case) between two adjacent longitudinal sections. In greater detail, the ability to provide a plurality of negative locked states between two segments is achieved by adapting/embedding a linear ratchet mechanism in to axial slip joints. The mechanism comprises of three main parts, a linear rack 404, a pawl 405 and a tension element 406 (spring). A linear rack 404 with a line of uniform but asymmetrical tooth, having a moderate slope on one edge and much steeper slope on the other edge, is illustrated (FIGS. 14 and 15). When the teeth are moving in the unrestricted direction (circumferential expansion for this particular case) the pawl 405, easily slides up over the gently sloped edges of the teeth. The spring 406 constantly forces the pawl 405 into depression between the teeth 404. When the teeth move in the opposite direction, however, the pawl will catch against the steeply sloped edge of the first tooth it encounters, thereby locking it against the tooth and preventing any further motion in that direction. FIG. 15, illustrate the mechanism in an unlocked state caused by presence of external pressure 407, applied to counter the push force of the spring 406, eventually lifting the pawl and unlocking the mechanism. Alternatively, a similar spring loaded with mechanism without the sliding teeth but with regular homogenous locking teeth could be easily adapted.

Figure 16:
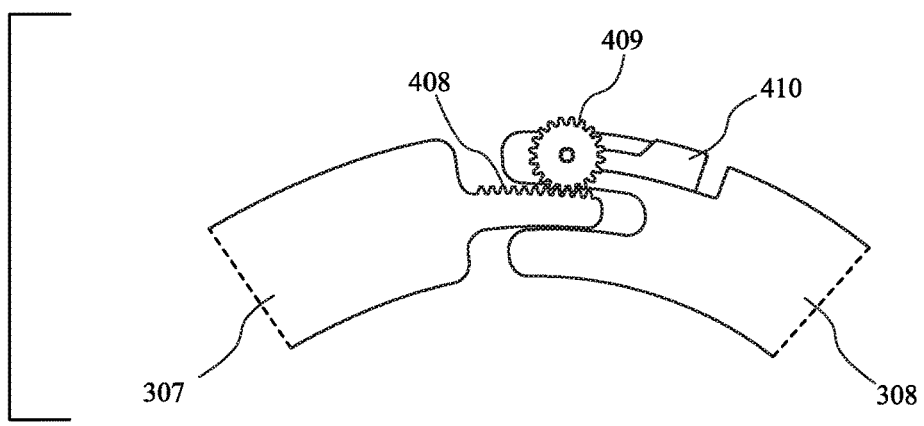
Figure 17:
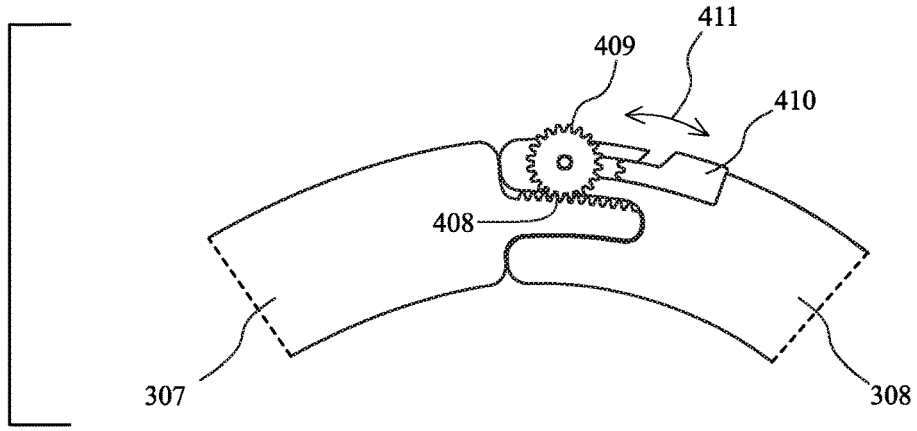

In another embodiment, an improved locking mechanism with multiple completely locked states is illustrated in FIGS. 16 and 17. The improvement involve the adaptation of a rack and pinion type of actuator to allow a number of locked states for circumferential adjustment (increase or decrease). In greater detail, the ability to enable/control circumferential expansion and contraction with a number of completely locked states between two segments is achieved by adapting/embedding a rack and pinion type of actuator in to axial slip joints. The mechanism comprises of three main parts, a linear gear called the rack 408, a circular gear called the pinion 409 and a break system 410. A linear rack 408 with a line of uniform symmetrical tooth is aligned with a circular gear 409 located on the adjacent segment of an axial slip joint. The rotational motion applied to the pinion causes the rack to move relative to the pinion, thereby translating the rotational motion of the pinion into linear motion or the opposite. A sliding lock mechanism 410 is also introduced to lock or unlock the system. FIG. 16 illustrates the system in a locked state with the sliding 411 lock 410 blocking circular motion of the pinion 409 and eventually blocking circumferential adjustment of the rack 408. FIG. 17 illustrates the system in an unlocked state with a sliding lock 410 not interfering with the circular motion of the pinion 409 and thus circumferential adjustment of the rack 408. Alternatively, a circular ratchet mechanism with a circular rack with asymmetrical tooth, a pawl and a tension spring could easily be adapted to allow circumferential increase while being in a negative locked state.

Figure 18:
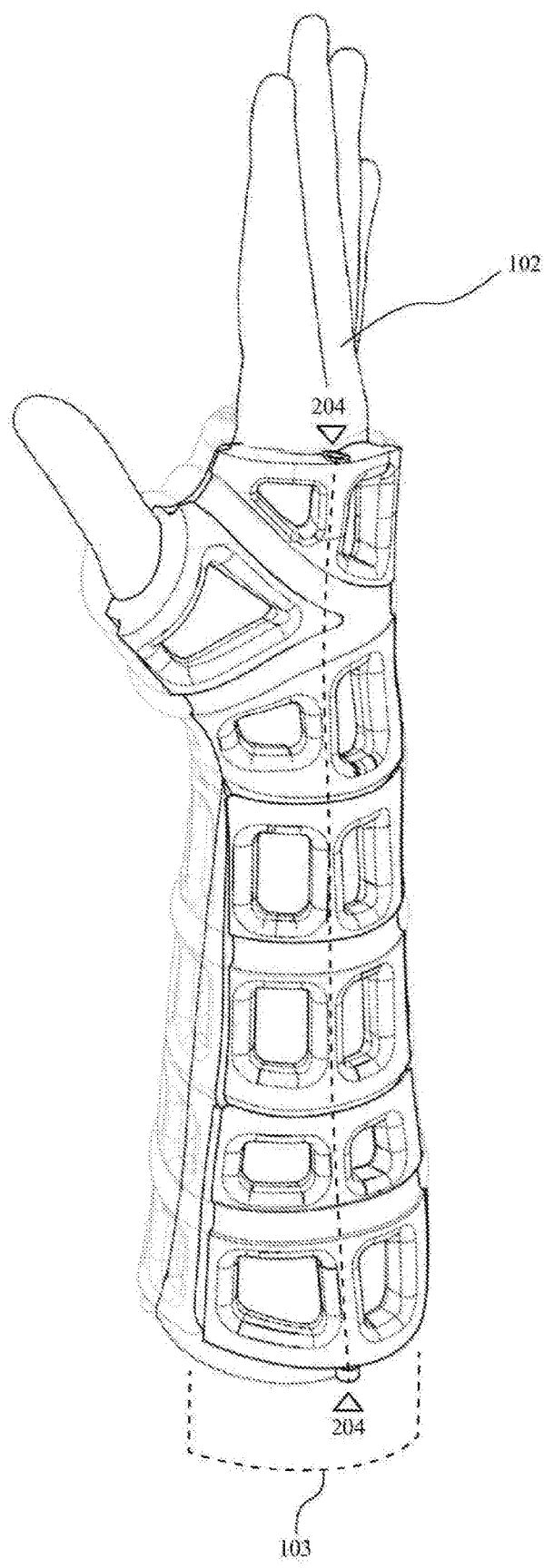
FIG. 18 is a personalized splint with circumferentially split segments held together by an axial tether.

Post-fracture edema accumulation, followed by atrophy are unescapable dynamics in fracture management. Effects of edema accumulation and atrophy are most intense in areas where muscle density is highest, typically resulting in uneven swelling or shrinkage within the body scaffold. The overall circumferential adjustment capabilities and medical performance of a portion or portions of longitudinal segments will significantly improve by further dividing the body scaffold in transverse axis into a plurality of longitudinal sections (two, three, four or more) making each subjected cell being part of a radial (circumferential) and axial (longitudinal) portion simultaneously. The components of a longitudinal portion are held together through structural modifications of cells and introduction of at least one axial tether mechanism with sufficient compressive force, pushing cells towards each other. The longitudinal portion 103 (FIGS. 1 and 18) of an upper extremity splint covering a section of human anatomy 102 is a typical embodiment of SMS with a plurality of circumferentially split segments. Section 204 (FIG. 18) is illustrated in FIG. 19 to provide greater detail regarding to the structure and dynamics of the system.

Figure 19:
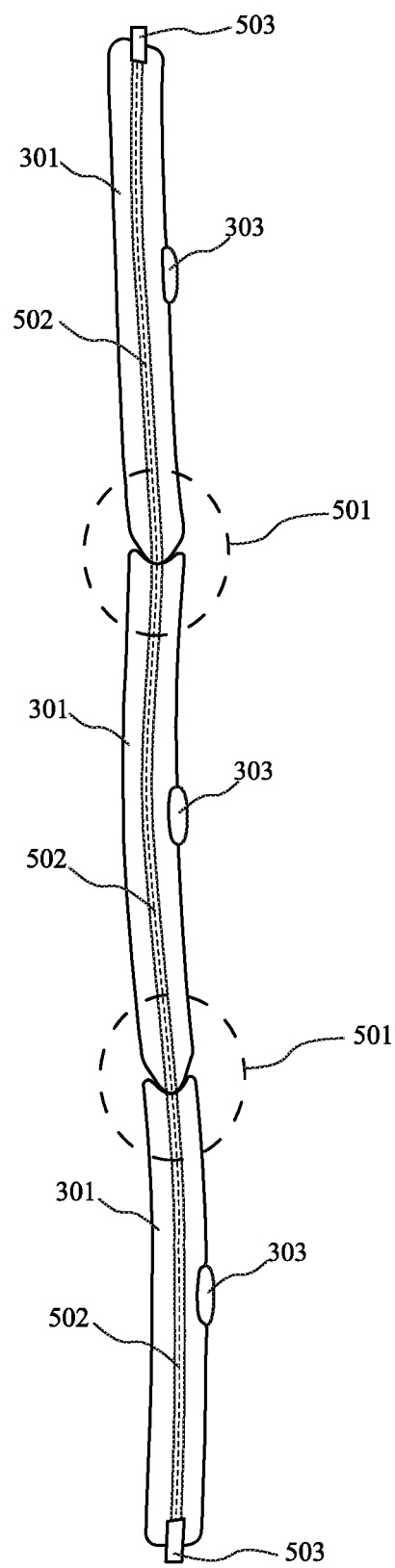
FIG. 19 is an axial cross-section of the splint of FIG. 18 showing placement of the tether.

FIG. 19 illustrates a longitudinal section with three circumferentially split segments. These three cells comprise a longitudinal portion (structure) which has three circumferential slip joints 501 located between adjacent cells. Male or female slip joint topology may exist on each end of each circumferentially split segments. Circumferential slip joints 501, align each individual cell 301 in their longitudinal axis. The structure is held together with the support of at least one additional axial constraining mechanism, constantly pulling cells towards each other. The axial constraining mechanism consists of two elements. A first element comprises a string or wire-like tether 502 which passes through or on the surface of cells and connect each element in a longitudinal axis. This wire-like constraint 502 is also observable in FIG. 3. The wire like constraint may take the form of a wire, a line, a string with flexible, inflexible or partly flexible material characteristics. A plurality of anchoring elements 503 or points fix the wire-like axial tether and cells together. Rather than passing through the cells with one single element, a plurality of cells corresponding a longitudinal structure can be linked through a series of wires and anchors reaching the same effect for subdivided structures. The anchoring elements 503 are located in proximal and distal end of the body scaffold and may take the form of designated design solution(s) within the cells or embodied as external elements with screws or gears for tension adjustment capabilities.

Figure 20:
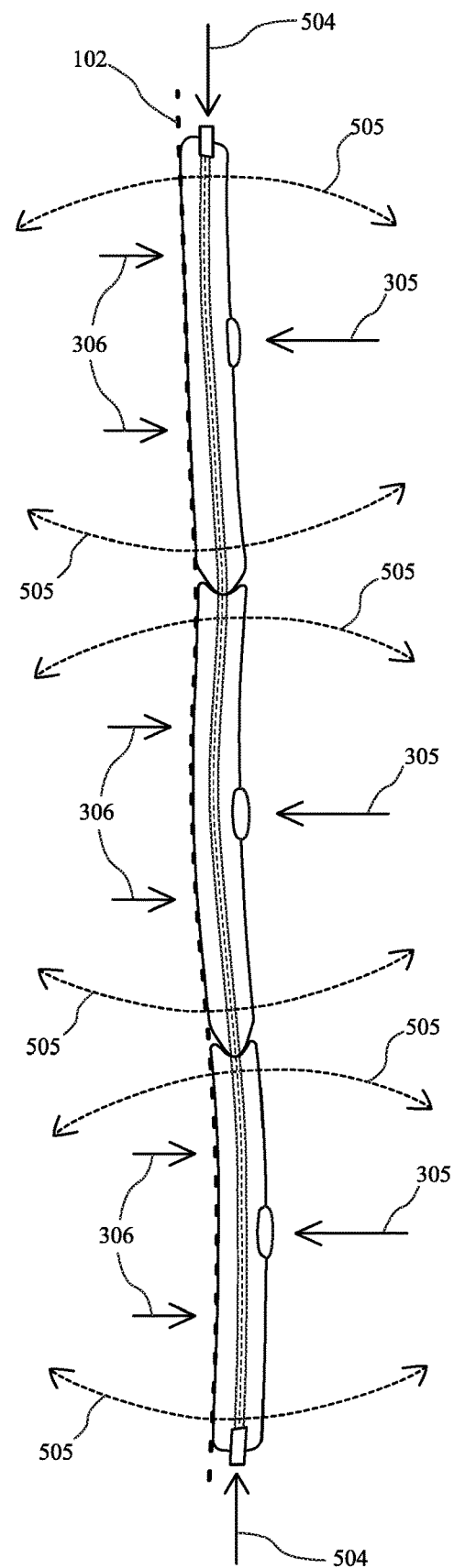
FIG. 20 is an axial cross-section of the splint of FIG. 18 with illustrations of internal dynamics of the system.

FIG. 20 illustrate the physical forces and self-alignment capabilities observed in the same section (section 204 and FIG. 19). The compressive force 504 generated by the axial constraint mechanism (axial tethers), combined with circumferential slip joints 501 hold the longitudinal structure 103 intact. Furthermore, the circumferentially inward force generated by a radial elastic restraining element (illustrated in FIG. 3 as 305) is also illustrated in this figure as a single horizontal force pushing each cell towards patent anatomy (102). The radially outward force generated by the patient anatomy or the locked state of axial slip joints, (illustrated in FIG. 3 as 306) is also illustrated in this figure as a series of horizontal forces pushing each cell on the opposite direction. In the case of an edema accumulation or atrophy or any significant change in the patient anatomy, each circumferentially divided cell of the longitudinal group has the capacity to rearrange its position according to the modified patient anatomy and adjacent cells. As a longitudinal structure with a plurality circumferentially divided cells, circumferential slip joints and an axial tether, the dynamics of the system resemble a folding white cane typically used by the visually impaired. 505 illustrates rotational paths for self-alignment of each individual cell in a longitudinal group. The range of motion (rotational capability) of each cell can be regulated by modifying circumferential slip joint topology 501.

In an embodiment, alternative circumferential slip joint topologies can regulate range of motion of a cell in its axis, implementations of different design solutions are disclosed over section 204 in FIGS. 21, 22, 23, 24, 25 and 26. The improvement involve different male and female circumferential slip joint topologies (501) for regulating (limiting) the dynamics of a longitudinal group. Male end of an individual cell in a longitudinal group (103) is illustrated with 506. Female end of an individual cell in a longitudinal group (103) is illustrated with 507.

Figure 21:
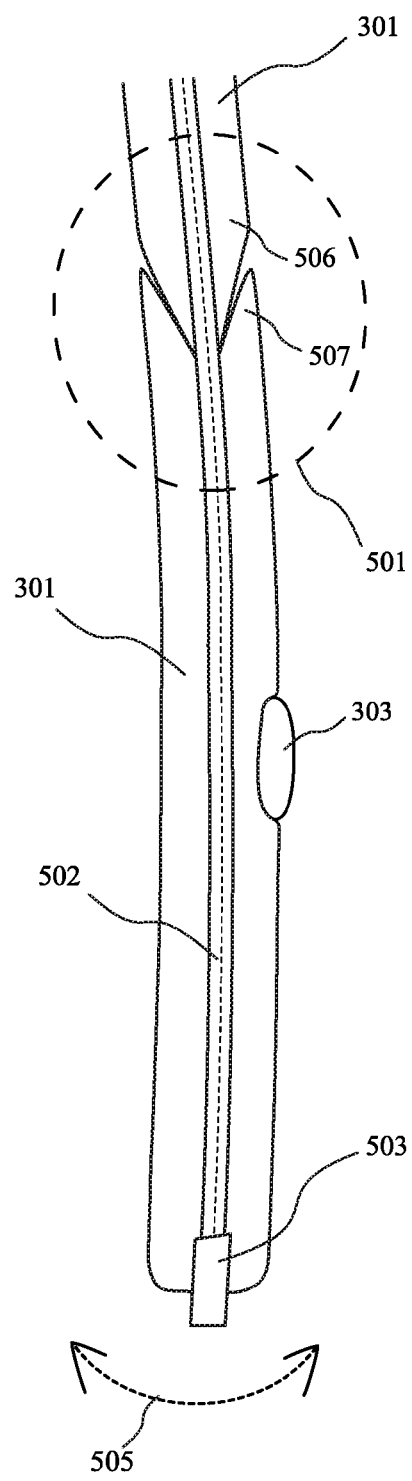
FIGS. 21-23 are axial cross-sections of a circumferential V-type slip joint.
Figure 22:
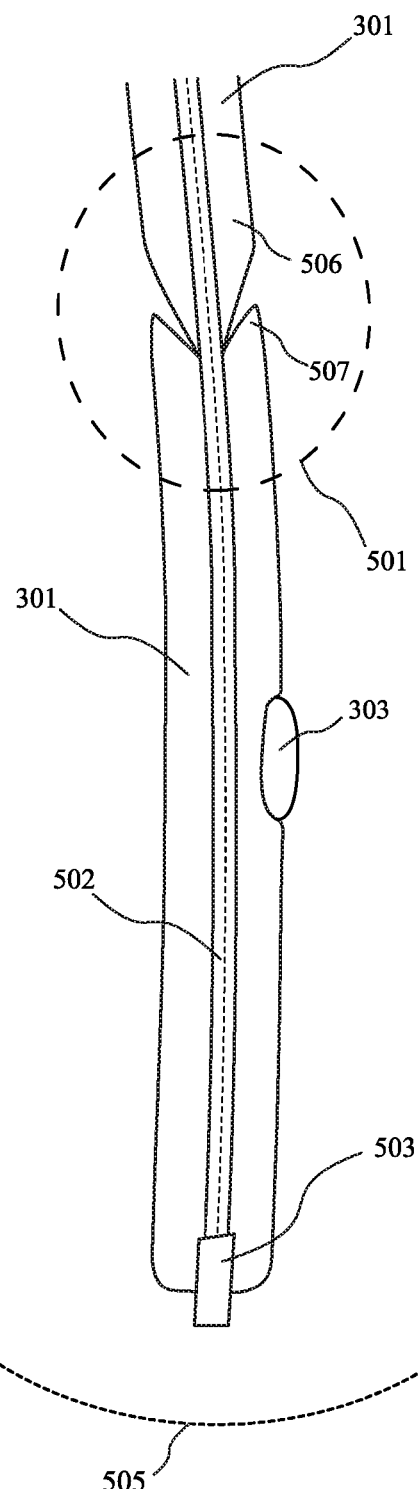
Figure 23:
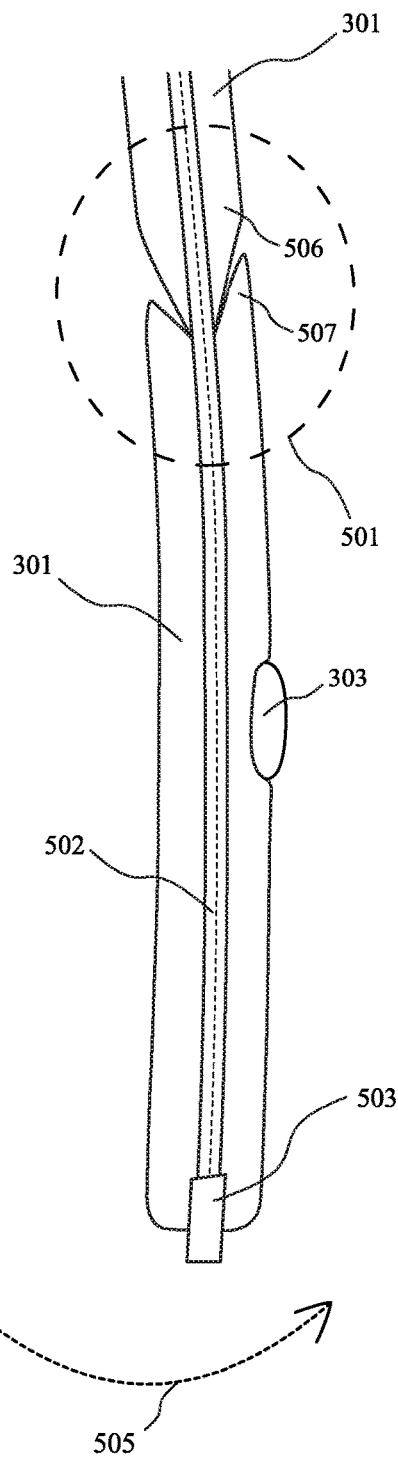

FIGS. 21-23 illustrate a "V" type (like) circumferential slip joint topology 501 between male 506 and female 507 ends of two circumferentially split adjacent segments. The "V" type circumferential slip joint topology is very convenient for limiting (regulating) the range of motion 505 between adjacent segments. FIG. 21 illustrates a very limited range of motion 505 due to very limited space between male 506 and female 507 adjacent segments. FIG. 22 illustrates an increased range of motion 505 due to an increased space between male 506 and female 507 adjacent segments. FIG. 23 illustrates an asymmetrical range of motion which is limited in one direction and extended in the opposite direction due to asymmetrical space between male 506 and female 507 adjacent segments.

Figure 24:
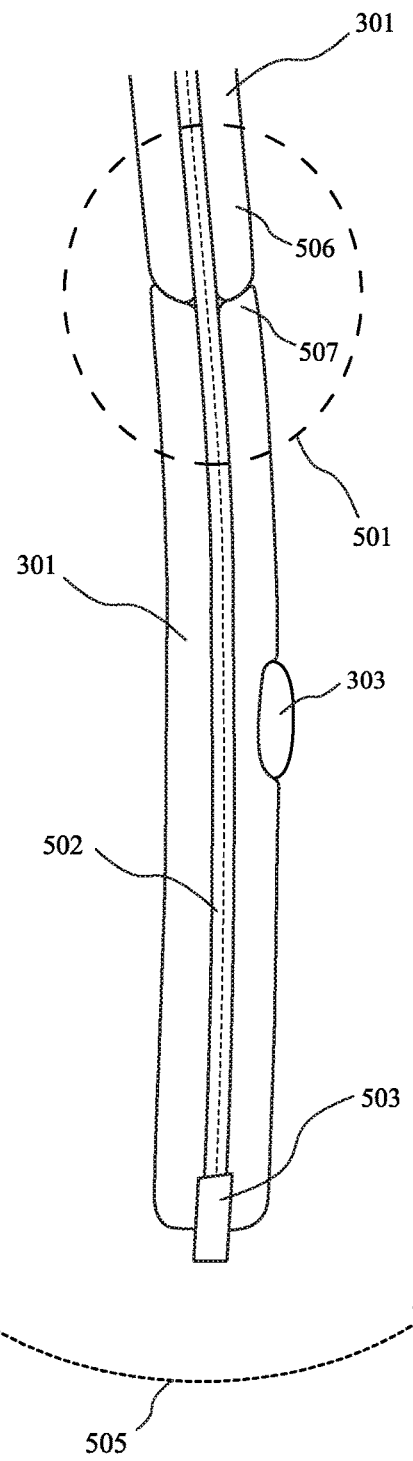
FIGS. 24-26 are axial cross-sections of a circumferential C-type slip joint.
Figure 25:
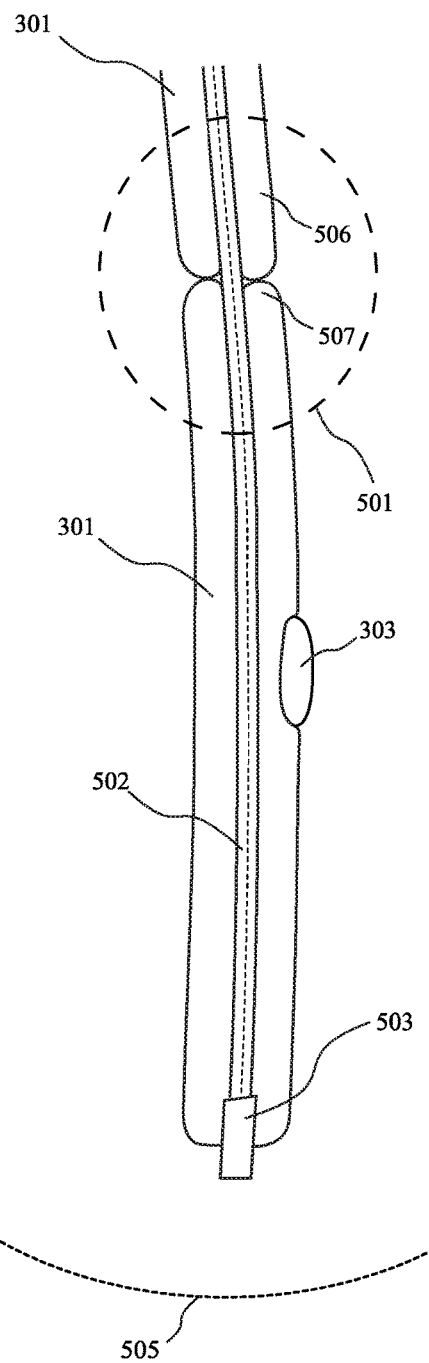
Figure 26:
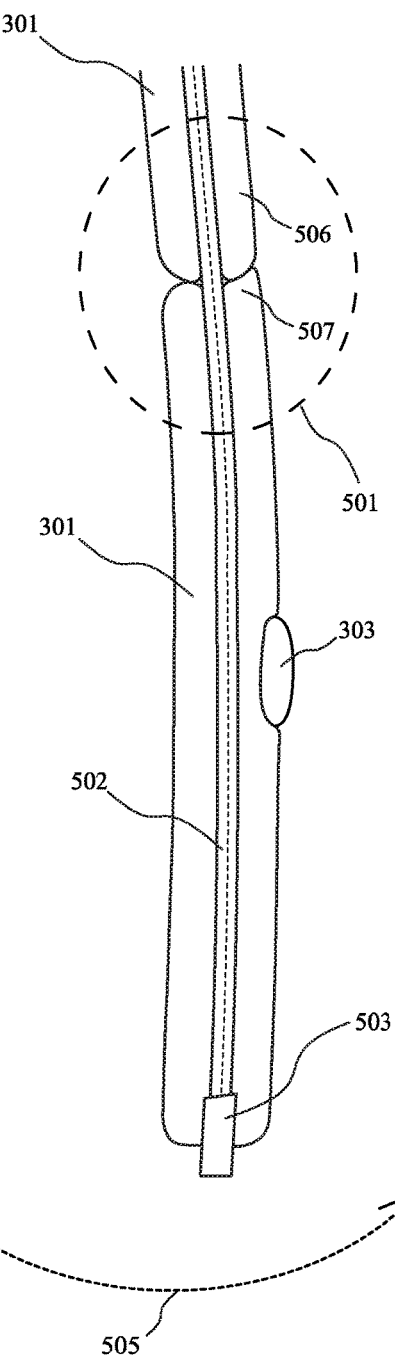

FIGS. 24-26 illustrate a "C" type (like) circumferential slip joint topology 501 between male 506 and female 507 ends of two circumferentially split adjacent segments. The "C" type longitudinal slip joint topology is very convenient for very large the range of motion 505 between two adjacent segments. FIG. 24 illustrates a larger range of motion 505 due to sliding space between male 506 and female 507 adjacent segments. Alternatively, the structure can evolve into a ball and socket type joint 510 as discussed in FIGS. 31 and 32. FIG. 25 illustrates an extremely increased range of motion 505 due to use of two "C" type male 506 adjacent segments. FIG. 26 illustrates an asymmetrical range of motion which is limited in one direction and extended in the opposite direction due to asymmetrical space between 506 and female 507 adjacent segments. Similar circumferential slip joint topology can regulate range of motion between adjacent cells with ease.

A stiffness prevention system (SPS) can be introduced as a supplementary method for SMS to enable and/or regulate anatomic motion in joints under orthotic intervention. SPS is implemented through first structural modifications to circumferential slip joints in order to physically allow such desired motion. Second, precise positioning of the elements around anatomic joints allows such a desired anatomic motion. Finally, the axial tether mechanisms may be adjusted in order to regulate such motion. Desired anatomic motions include flexion, extension, abduction, adduction, pronation, and supination. SPS is explained between two circumferential portions of an upper extremity splint 101 and 104 covering a wrist, is a typical embodiment of SPS. Section 205 (FIG. 27) is illustrated in FIGS. 28, 29 and 30 to provide greater detail regarding the structure and dynamics of the system.

Figure 28:
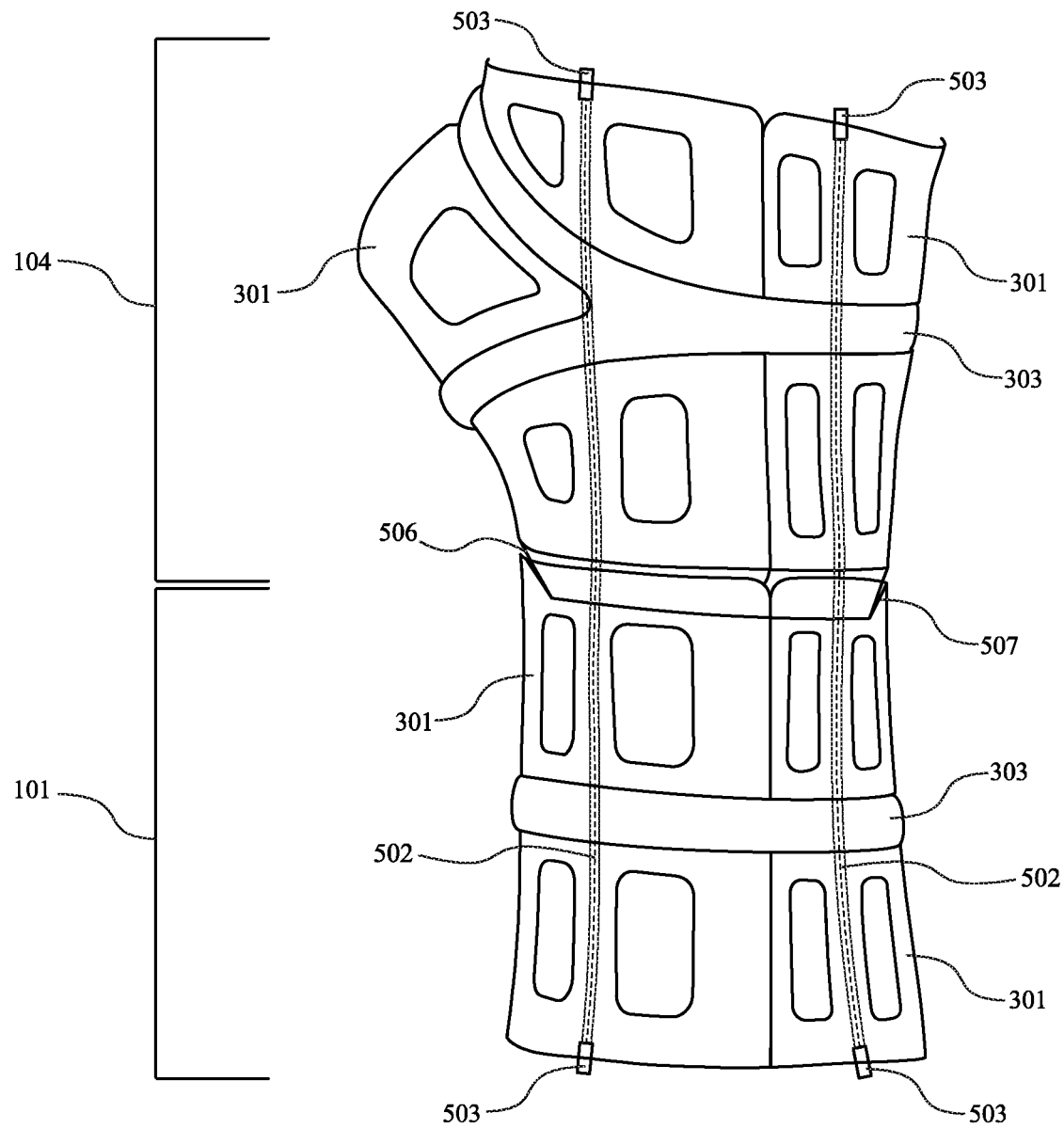
FIGS. 28-30 show the body scaffold of FIG. 27 in different degrees of bending.

FIG. 28 illustrates an embodiment of SMS without any structural modifications to circumferential slip joints 501 in order to incorporate SPS and can be referred as the default structural state of the system. In order to provide a stable and durable structure, circumferential slip joints 501 are flat and in full contact with each other.

Figure 29:
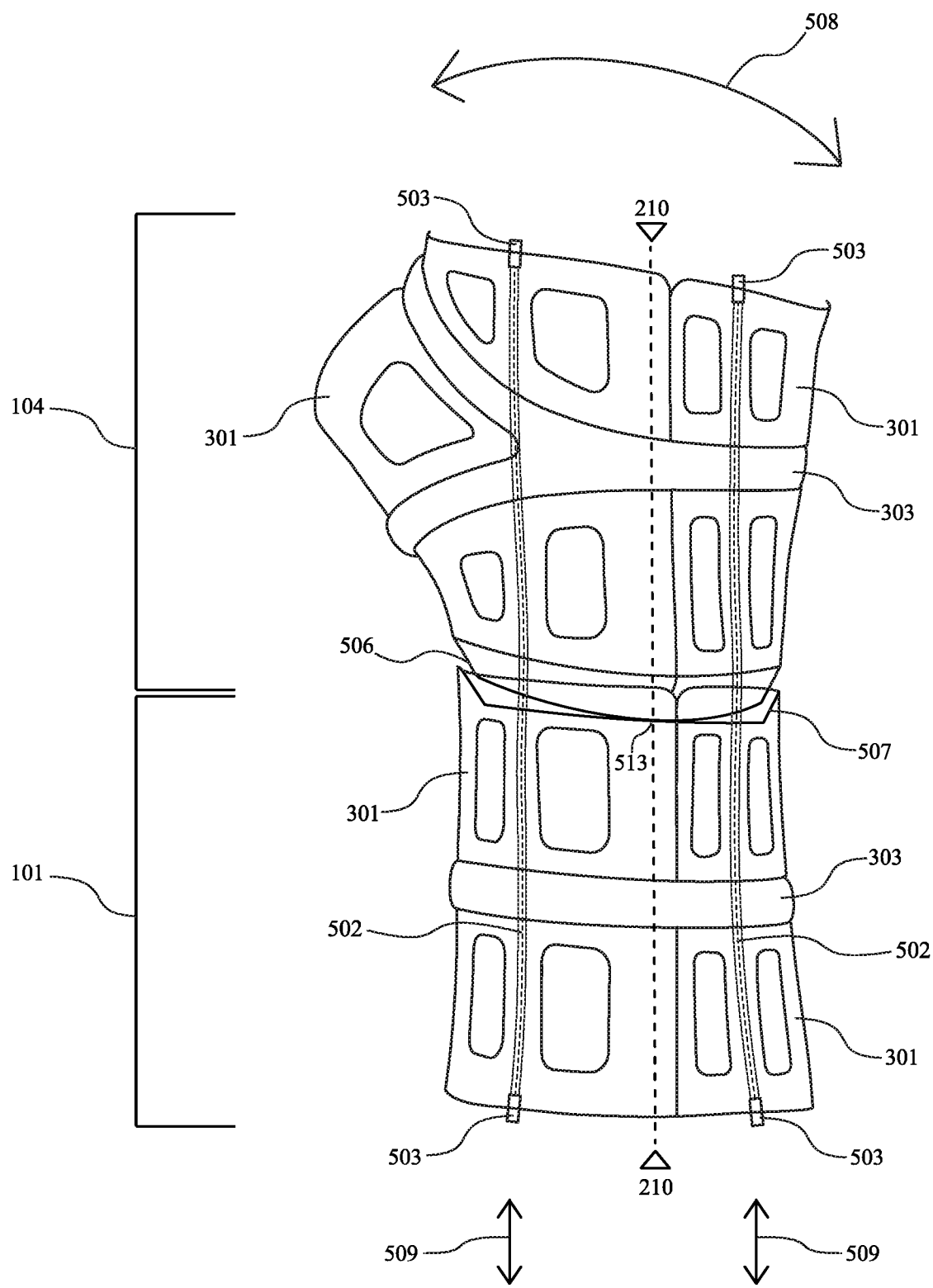
Figure 42:
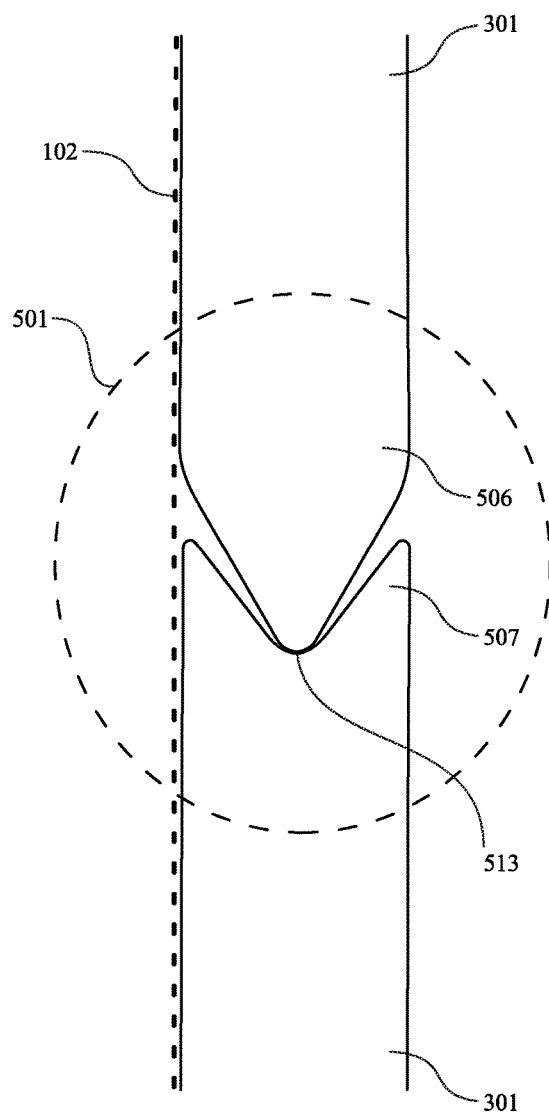
FIG. 42 is an axial cross-section of the circumferential slip joint of splint of FIG. 29 illustrating the minimal tangential relationship between two circumferential portions.

In an embodiment, illustrated in FIG. 29, two circumferentially split segments 101, 104 of a body scaffold are configured to axially separate in order to regulate anatomic motion 508 (such as bending of a joint). The fitting full contact relationship between the two components of a circumferential slip joint 506, 507 is modified to allow pivoting between the segments. Section 210 is illustrated in FIG. 42 to provide greater detail regarding the structure of slip joints 501. It is advantageous that a minimal tangential contact area 513 be maintained between the two circumferential portions over a body joint to physically allow the desired anatomic motion. Anchor points 503 (FIG. 29) play a key role in regulating anatomic motion since increasing or decreasing tension 509 of axial tethers 502 will inevitably rearrange the position and the angle between the segments of the body scaffold.

Figure 30:
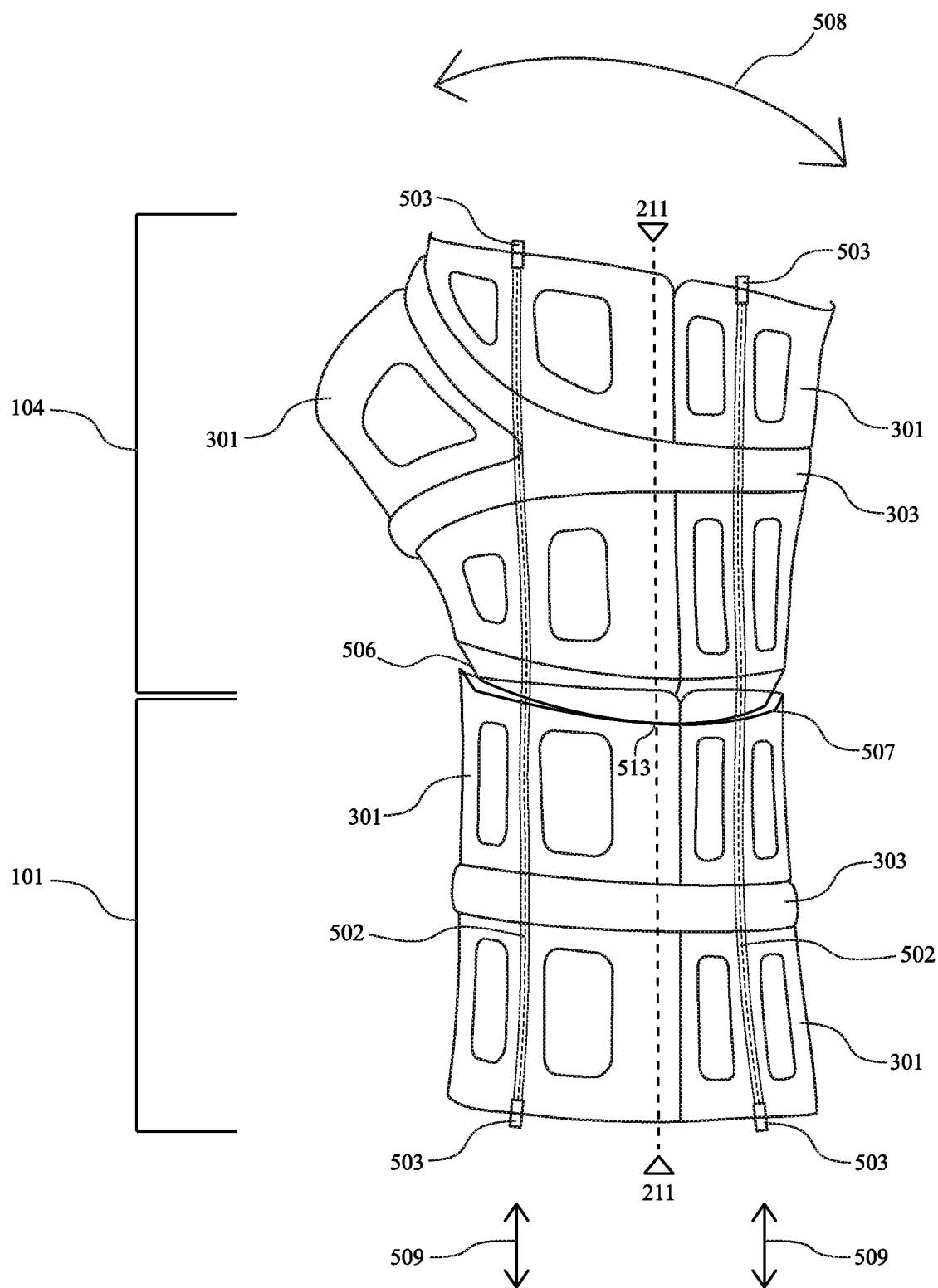
Figure 43:
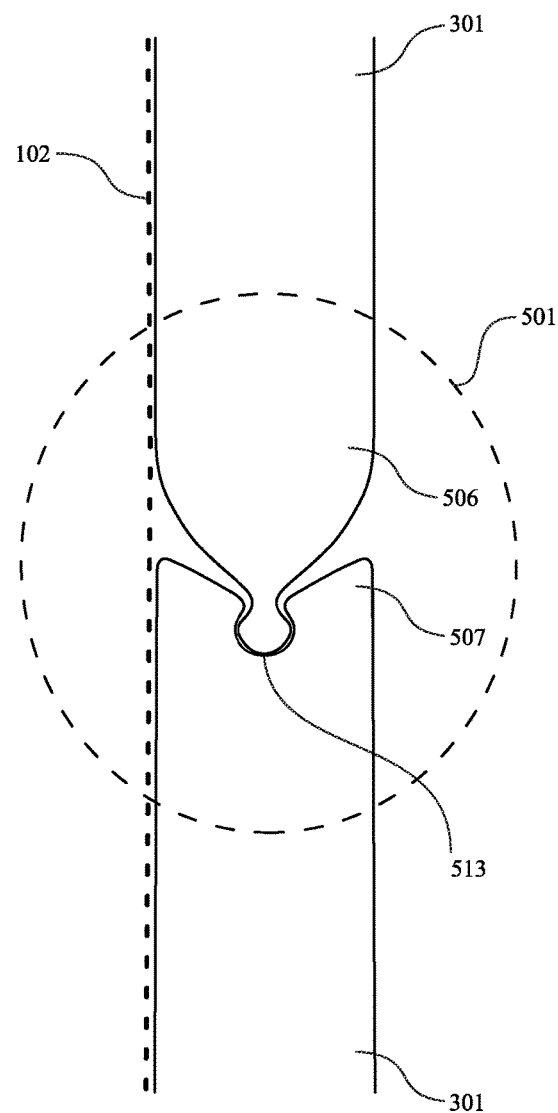
FIG. 43 is an axial cross-section of the circumferential slip joint of splint of FIG. 30 illustrating the sliding rail topology between two circumferential portions.

In an embodiment, as illustrated in FIG. 30, two circumferentially split segments 101, 104 of a body scaffold are configured to axially separate in order to regulate anatomic motion 508 (such as bending of a joint). The fitting full contact relationship between the two components of a circumferential slip joint 506, 507 is modified to allow sliding between the segments. Section 211 is illustrated in FIG. 43 to provide detail regarding the structure of slip joints with sliding rail type topology between male 506 and female 507 slip joints. It is essential that the sliding rails between the two circumferential portions, are placed over a body joint to physically allow the desired anatomic motion. Anchor points 503 (FIG. 30) play a key role in regulating anatomic motion since increasing or decreasing tension 509 of axial tethers 502 will inevitably rearrange the position and the angle between the circumferential portions of the body scaffold.

Figure 31:
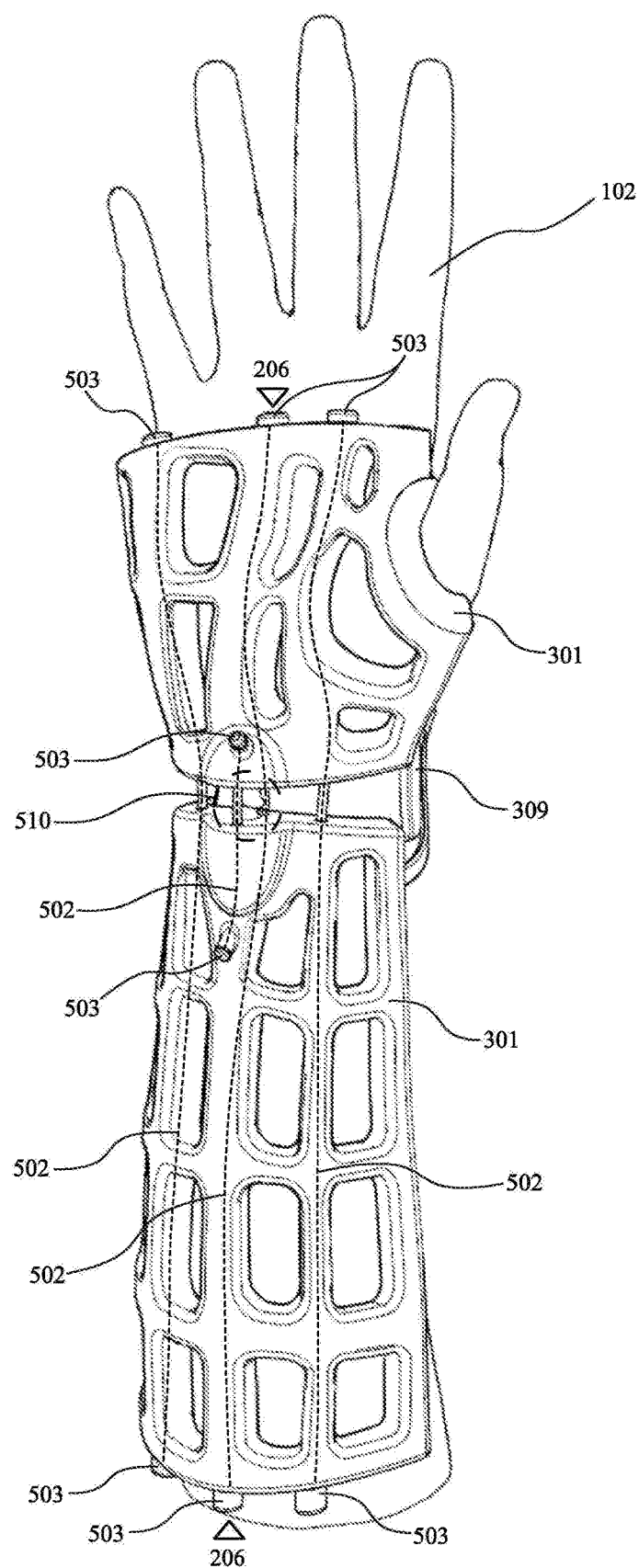
FIG. 31 illustrates a half body scaffold with SPS with a plurality of axial tethers and a ball joint serving as a circumferential slip joint.
Figure 32:
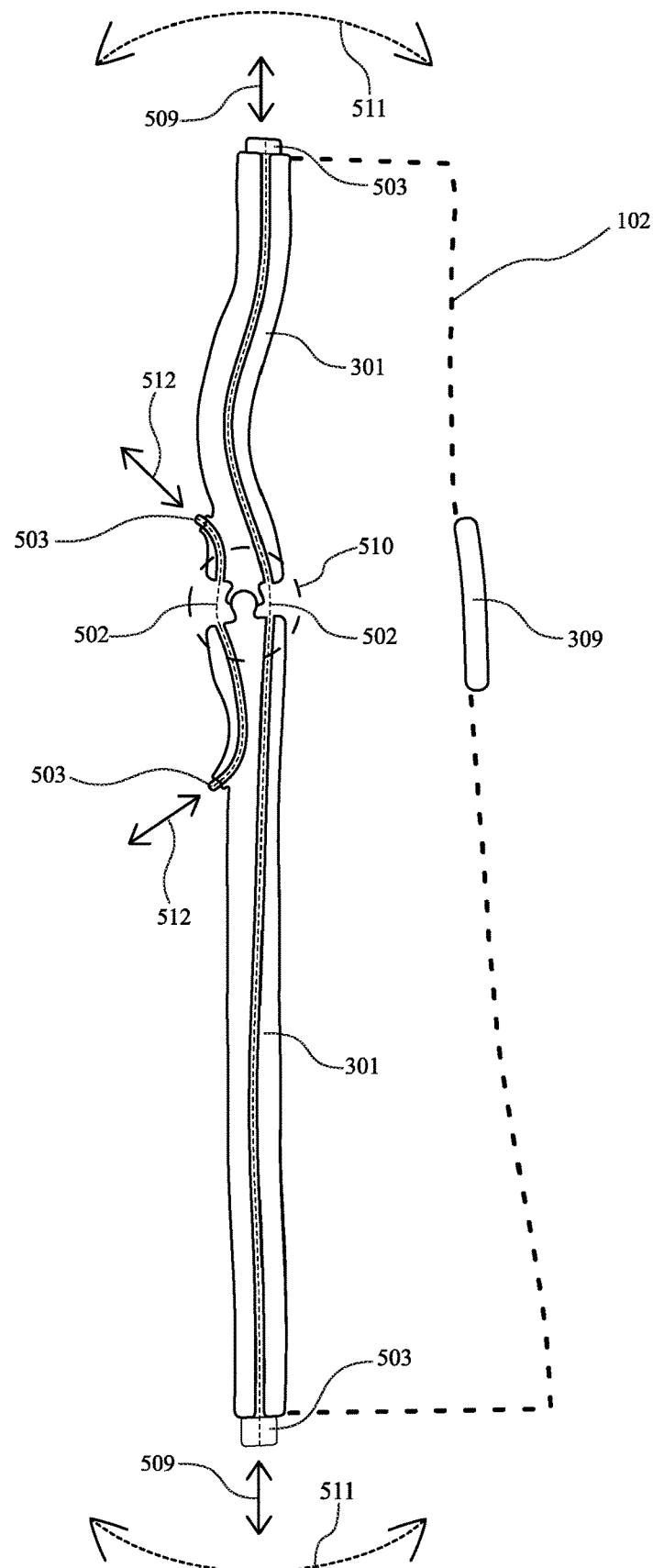
FIG. 32 is an axial cross-section of the half body scaffold of FIG. 31

Alternatively SPS can also be introduced as an independent system incorporating the related longitudinal alignment mechanism described in SMS in order to enable and regulate anatomic motion to desired joints in a half body scaffold. In an embodiment, a plurality of longitudinal restraining mechanisms are implemented to regulate anatomic motion with the use of at least one additional ball joint between portions of a half splint, are illustrated in FIGS. 31 and 32. FIG. 31 illustrates a half splint consisting of two cells (301), four longitudinal restraining elements (502) attached to two adjustable anchoring elements each (503), a ball joint (510) as an embodiment of longitudinal self-aligning slip joint topology (501) and a padding unit (309) to support patient anatomy (102).

The ball joint between two segments enable an extremely flexible range of motion between the elements and must be regulated with a plurality of axial tether mechanisms. For this particular embodiment, the axial tether mechanisms can be grouped in to two groups. The first two of the axial tether mechanisms are intended to regulate ulnar and radial deviation and are positioned on the sides (lateral and medial) of the body scaffold, the dynamic effects of these two restraining elements are similar to the dynamics described in FIGS. 29 and 30. The second two of the axial tether mechanisms are intended to regulate flexion/extension 511 and are positioned on the central axis of the body scaffold. Section 206 is illustrated in FIG. 32 to provide greater detail regarding the structure and the dynamics of the system. A ball joint 510 enables motion between two segments around the anatomic joint of the patient. Two axial tethers 502 are positioned at both sides of the ball joint to regulate desired motion 511. A tension of the axial tether mechanism may be adjusted by cinching the anchor points 503 along the axis of adjustment for each element is illustrated with 512.

Other motion regulating structures such us different kinds of joints and rails can be adapted between two portions for a variety of anatomic motions. The essentials of the system are placement of slip joints, ball joints and slots within the body scaffold to match the location of anatomic joints and the use of axial restraining mechanisms described in SMS in order to regulate motion.

The invention also incorporates methods for applying external pressure through the orthotic. Typically, fractures require some level of external pressure in order to support to the injured area. This pressure helps stabilizing the area and also help the fracture to heal. Bones are piezoelectric structures in nature, and the transfer of ions is an important contributor to fracture healing. Conventionally, the external pressure is applied by a medical professional during casting of the splint and particularly during cast's solidification process. This pressure can be applied to the fractured anatomic location by the medical professional in the same manner. Due to the nature of conventional applications there is also no way of measuring pressure or precisely defining the area for applying the pressure to the relevant areas.

Figure 33:
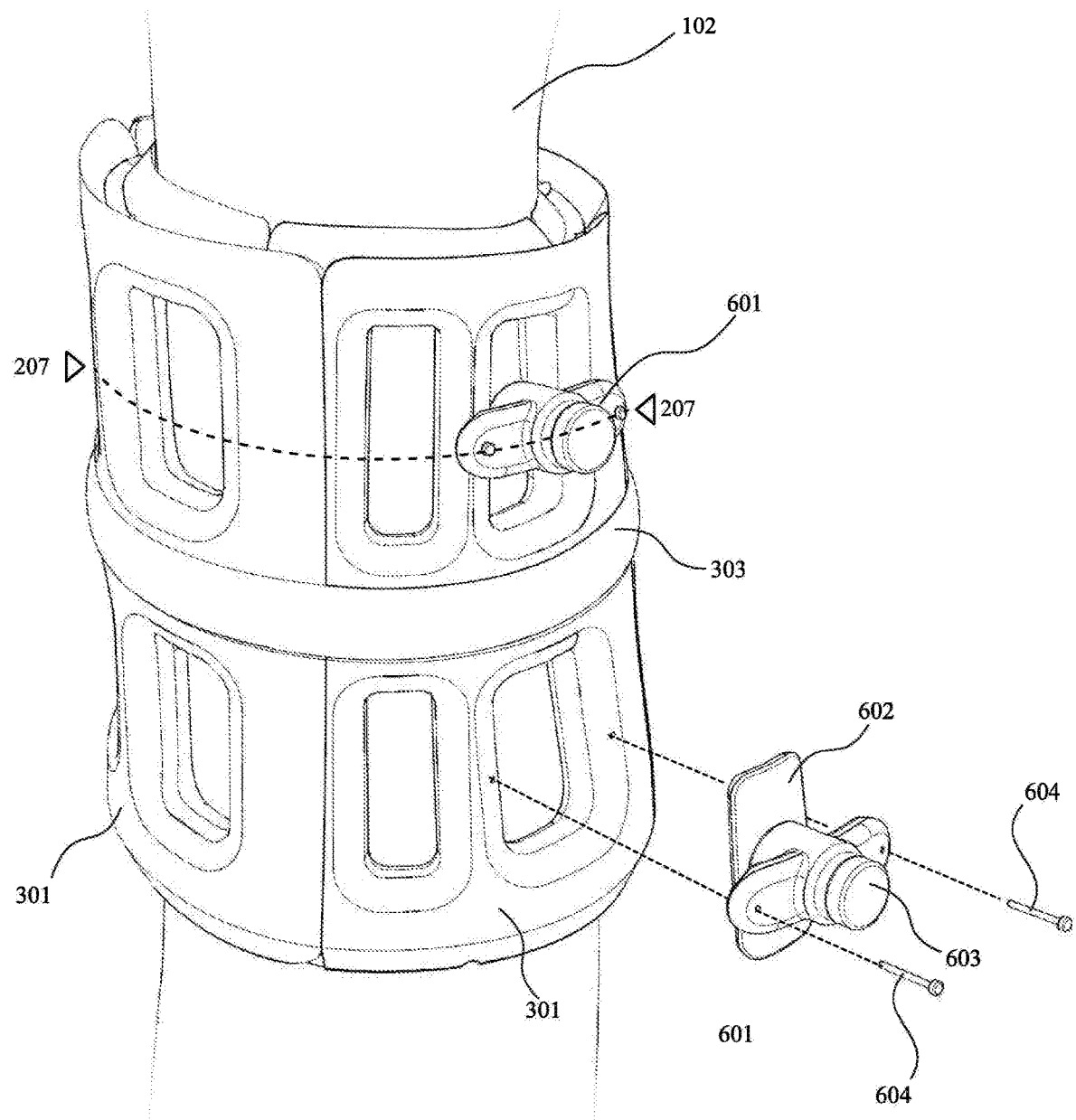
FIG. 33 illustrates two adjustable modular pressure units placed within a circumferential portion of a body scaffold with SMS.
Figure 34:
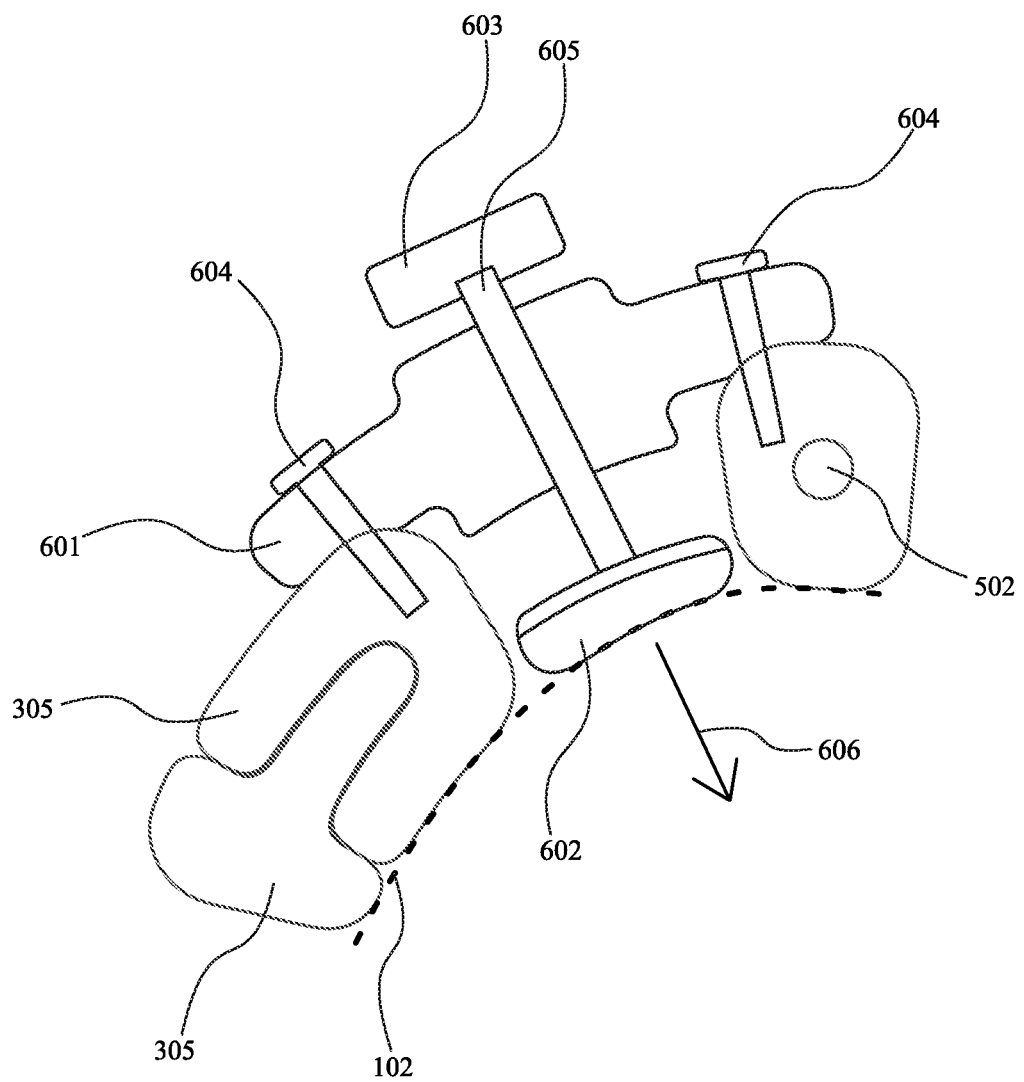
FIG. 34 is a transverse cross-section of an adjustable modular pressure unit attached to a circumferential portion of a body scaffold with SMS.

In an embodiment external pressure to patient anatomy can be applied through modular and adjustable pressure units. FIG. 33 illustrates two modular and adjustable pressure units attachable to a portion of a body scaffold with or without SMS. The body of modular and adjustable pressure unit 601 maybe 3D printed or produced with conventional manufacturing technologies. The area delivering pressure to the patient anatomy 602 is formed from a soft rubber-like viscoelastic material and/or may be produced from layers of different materials with different mechanical and chemical properties. The knob 603 is for adjusting the pressure delivered to patient anatomy. The modular unit can be fixed to the body scaffold through screws 604 and/similar mechanical solutions such as magnets. FIG. 34 is a sectional view that provides more details regarding to the structure and the dynamics of the system. The screw type shaft 605 connects the knob 603 the main body of the pressure unit 601 eventually regulating the position of the interface element 602. The physical relationship between the interface element 602 and the patient anatomy 102 is illustrated with 606. Alternatively, the knob, shaft and interface element combination can be embedded inside the body scaffold for the same external pressure adjustment purposes.

Figure 35:
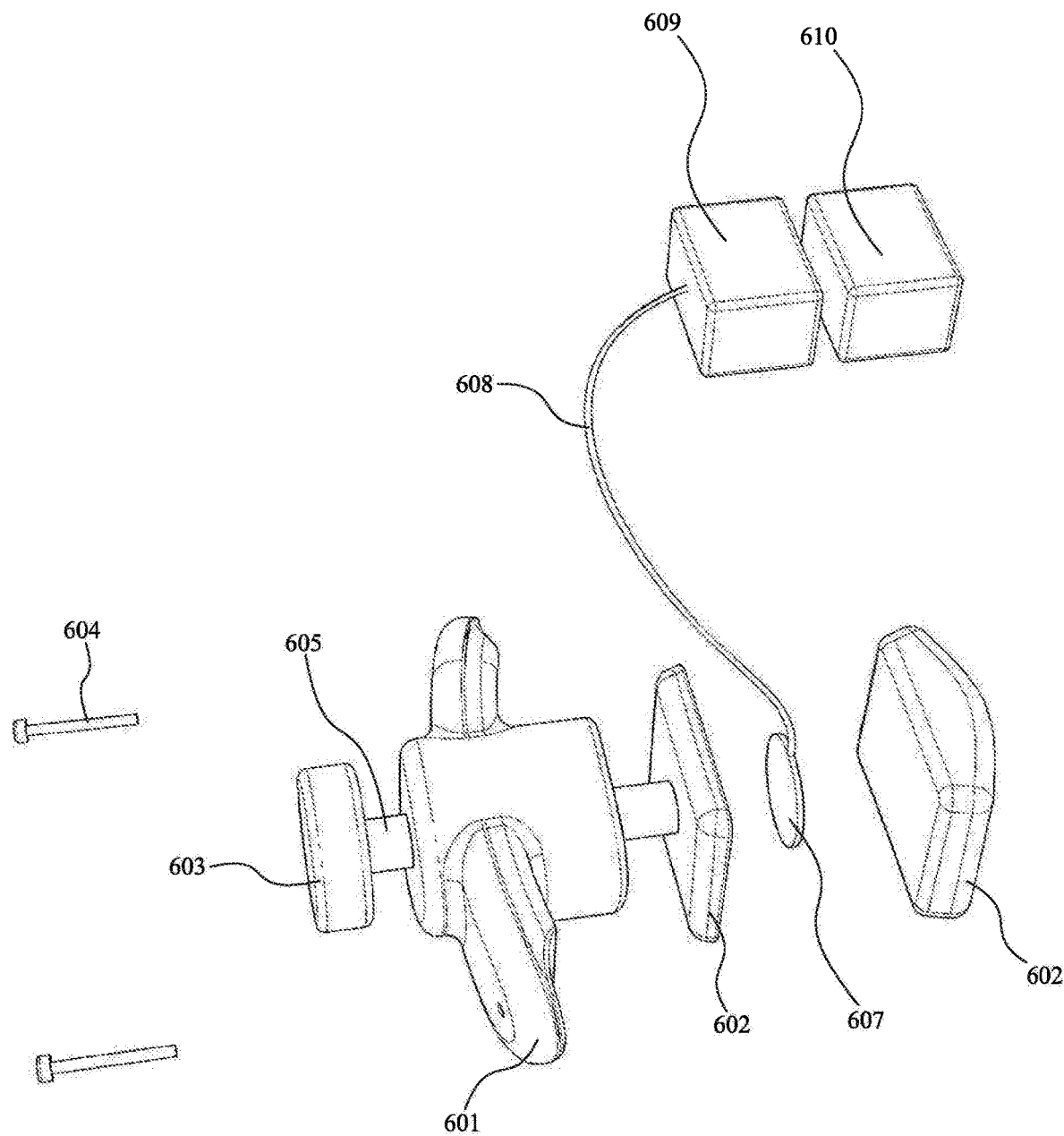
FIG. 35 is a blowup representation of an adjustable modular pressure unit with a pressure sensor.

In another embodiment, a pressure sensor is used to monitor the physical relationship between the modular adjustable pressure unit and the patient anatomy is illustrated in FIG. 35. The data mining feature is achieved by positioning (or embedding) a pressure sensor 607 between the layers of the interface element 602. The data mined by the sensor is transferred through a wire 608 connecting the sensor to a IOT device 609 with relevant computational and connectivity capabilities (an Intel Edison or Curie is a good example of such a device). The power source of the system is illustrated with 610 that may be a battery or a receiver for wireless energy transfer system. Alternatively, the knob, shaft, interface element and sensor combination can be embedded inside the body scaffold for the same external pressure monitoring purposes.

In another embodiment heat and cold to patient anatomy can be transferred trough modular pressure units is illustrated in FIG. 35. Heat can be generated using electrical resistors, thermoelectric generators, and the like. Thermotherapy (heat therapy) and cryotherapy (cold therapy) may be achieved by positioning (or embedding) a thermoelectric generator 607 between the layers of the interface element 602 for this particular application the section of the interface element in contact with patient anatomy must be from a highly thermo-conductive material also the section of the interface element in contact with the shaft 605 must be from a thermos-insulated material. The energy required for the application and controlling signal is transferred through a wire 608 connecting the thermoelectric generator to an IOT device 609 with relevant computational and connectivity capabilities (Intel Edison or Curie is a good example of such a device). The power source of the system is illustrated with 610 which may be a battery or a receiver for wireless energy transfer system (or similar power sources).

Rehabilitating any injury can be a time consuming and frustrating process. While the purpose of physical rehabilitation is to increase strength and flexibility, it usually ends prematurely before an injured area has been restored to its full pre-injury state. Massage plays an important role as a supplement to standard injury rehabilitation procedures. By encouraging circulatory movement and relaxing muscles, massage helps the body pump more oxygen and nutrients into tissues and vital organs. This allows the rehabilitating injured area(s) to become more flexible and heal at an accelerated rate.

Figure 36:
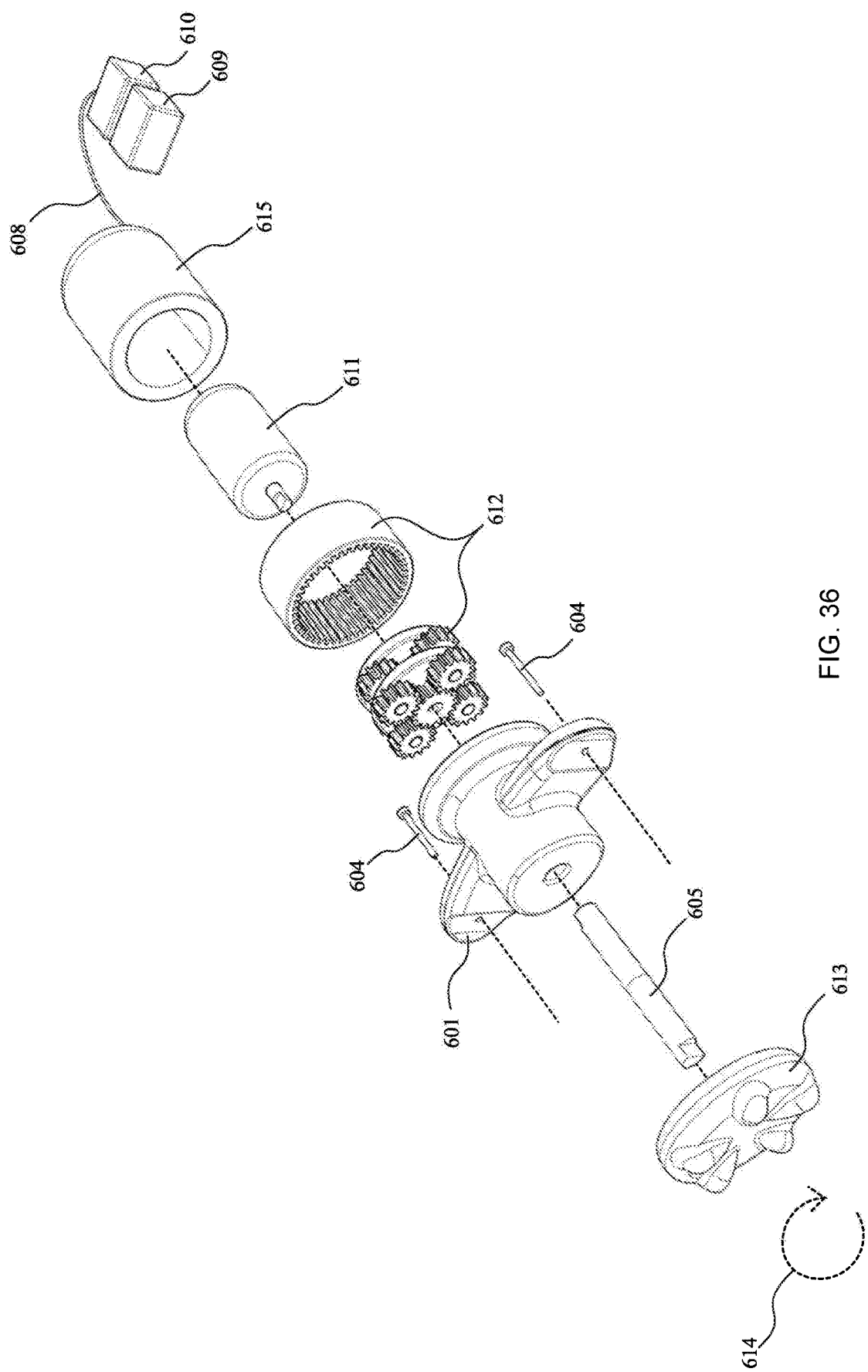
FIG. 36 is a blowup representation of an adjustable modular pressure unit with massage therapy components.
Figure 37:
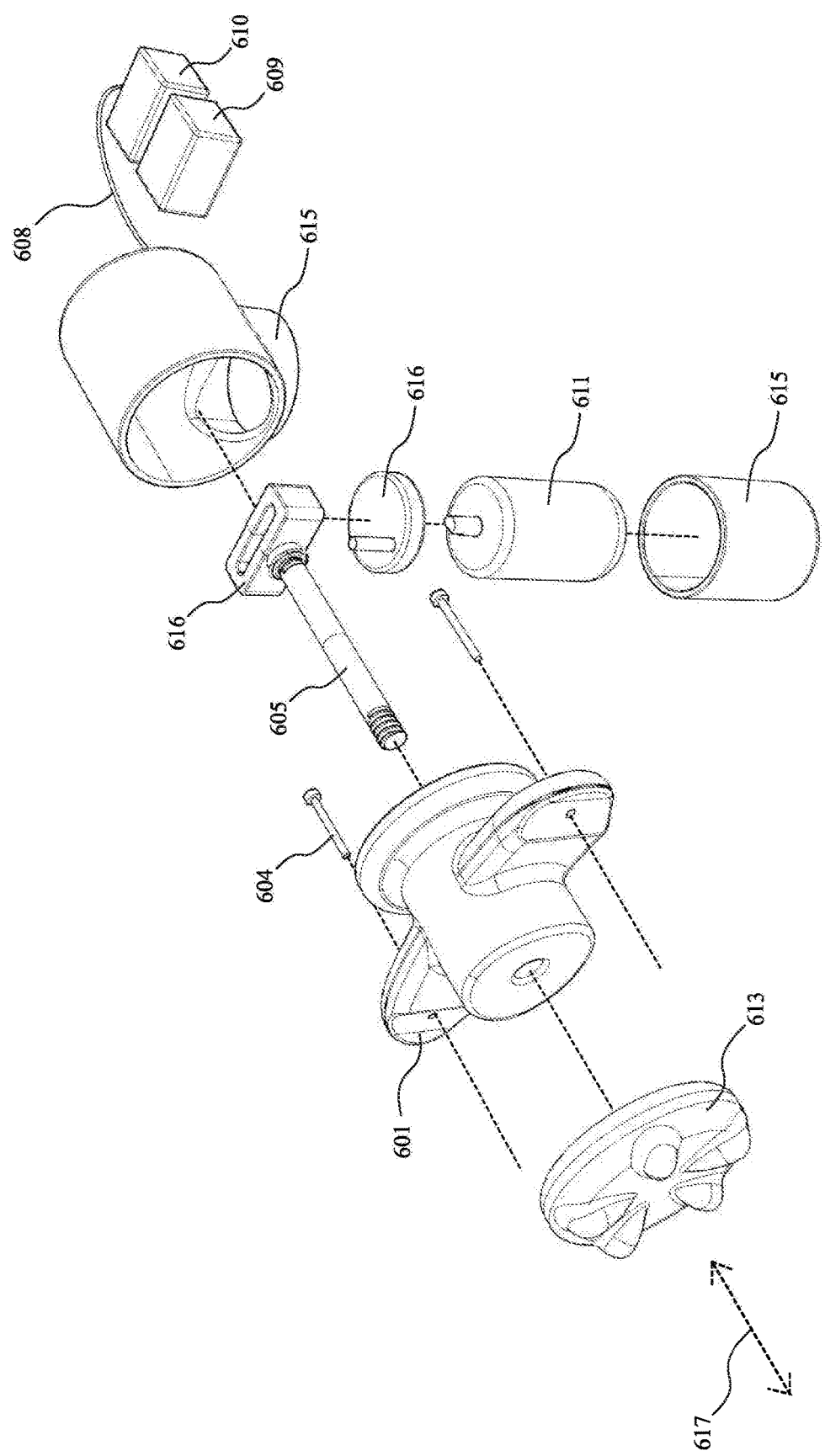
FIG. 37 is a blowup representation of an adjustable modular pressure unit with massage therapy components.

In an embodiment massage therapy could be applied to patient anatomy trough modular units. FIGS. 36 and 37 illustrates modular units with embedded electrical motors, mechanical parts and massage interfaces for delivering two kinds of massage therapy. FIG. 36 illustrates a blowup illustration of a modular unit with circulatory type of massage. The electrical engine 611 is positioned along a central axis of the unit and connects to a reduction gear 612 which reduces the rpm to increase the torque of the system. Rotational motion is transferred through the main body of the modular unit 601 via a shaft 605 to the massaging element 613, and the circular motion of the system is illustrated at 614. The system is fixed to a body scaffold via screws 604 (or other convenient mechanical solutions) and may be controlled by an IOT device 609 and/or directly connected to a power source 610. FIG. 37 illustrates a detailed illustration of a modular unit with punch type of massage. The electrical engine 611 is positioned perpendicular to the central axis of the unit connects to a Scotch yoke type of gear 615 which converts circular motion of the engine into a linear piston like up and down motion. Later linear motion is transferred trough the main body of the modular unit 601 via a shaft 605 to the massaging element 613 the up and down motion of the system is illustrated with 617. The system is fixed to a body scaffold via screws or similar mechanical solutions 604 and may be controlled by an IOT device 609 or directly connected to a power source 610. Other types of similar massage applications or techniques could be adapted using the similar methods and structures.

Figure 38:
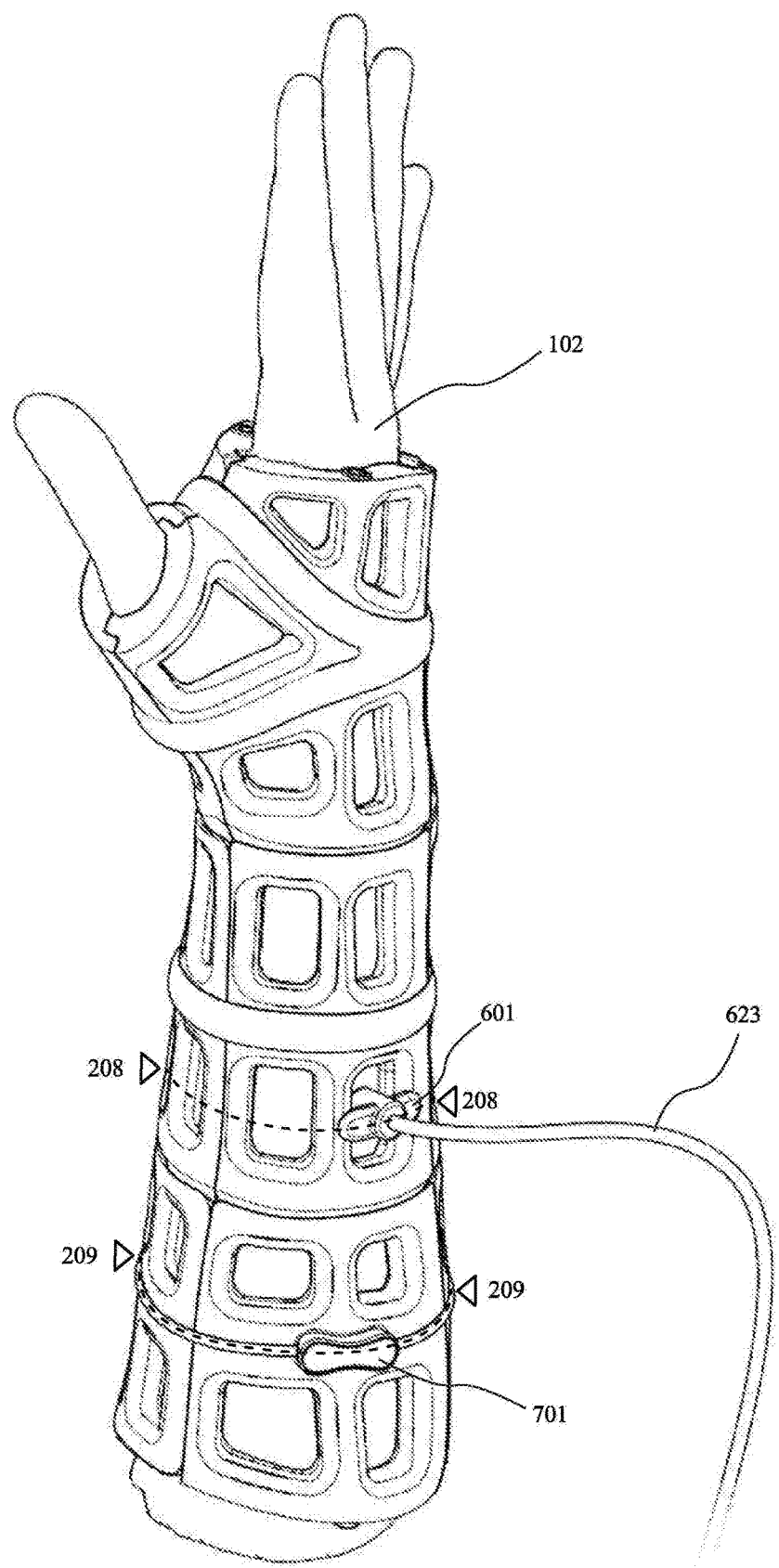
FIG. 38 is a body scaffold with a modular therapeutic unit and a circumferential sensor.
Figure 39:
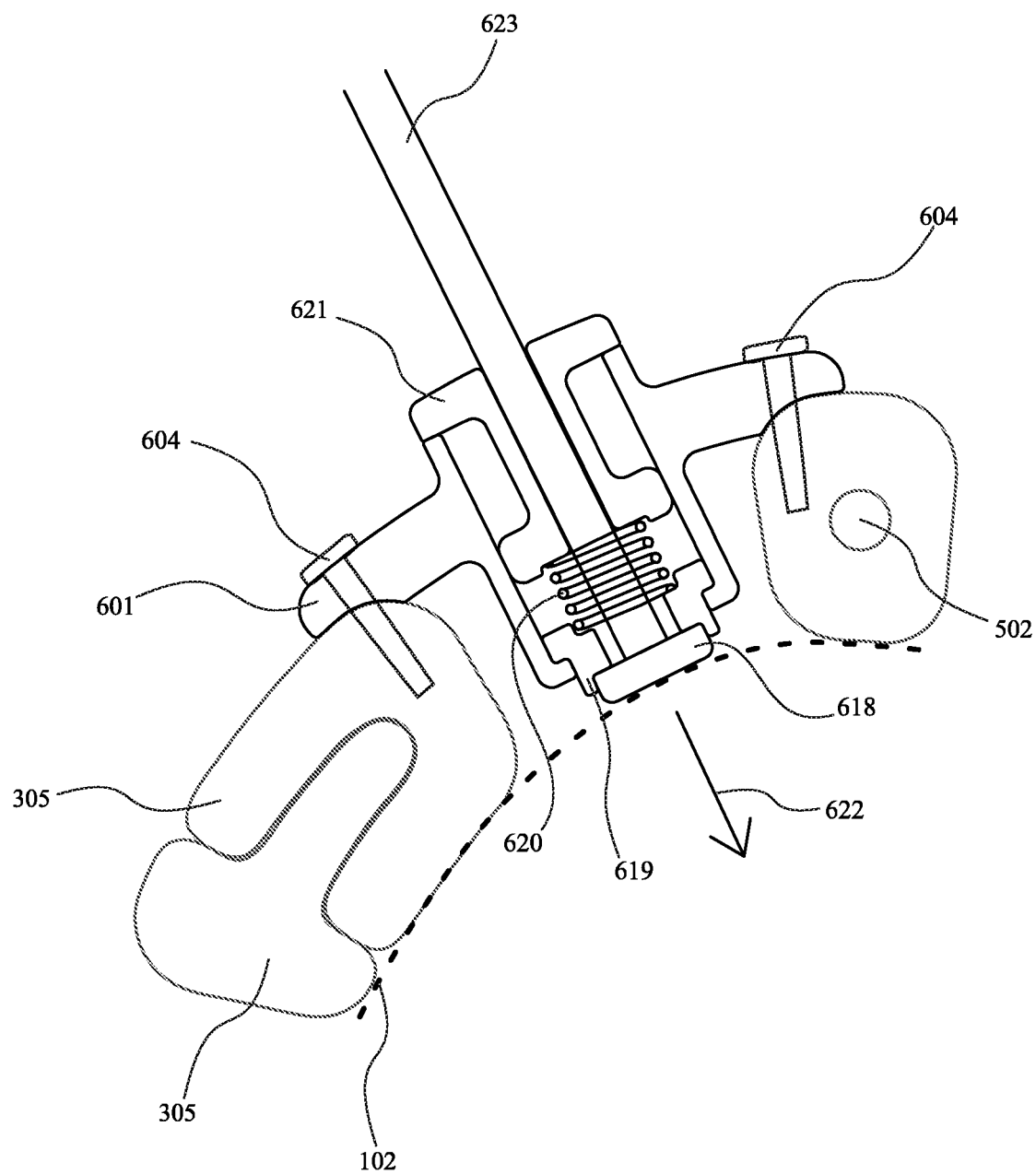
FIG. 39 is the section of a modular therapeutic unit attached to a portion of a body scaffold.
Figure 40:
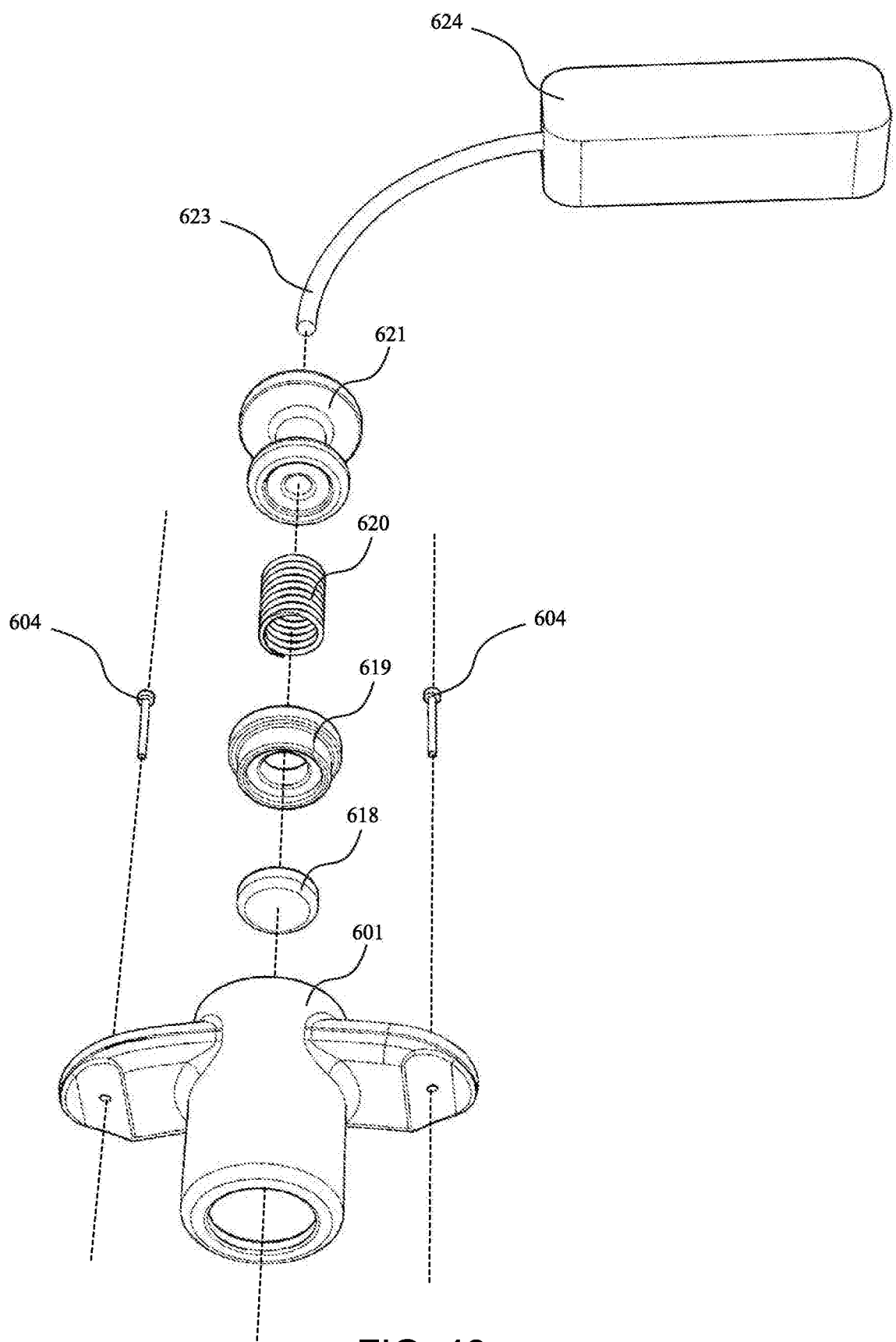
FIG. 40 is a blowup representation of a modular therapeutic unit

In additional aspects, the present invention provides a method for fabricating a comfortable body interface as a hub for therapeutic equipment. In some embodiments, the conformable interface element may further include a therapeutic element, a mechanism for pushing the therapeutic element towards the patient anatomy and an external electrical power source is illustrated in FIGS. 38, 39 and 40. A modular unit with the capacity to stabilize certain medically beneficial therapy delivering probes (effectors) to enable their usage during periods of orthotic intervention, a therapy delivering modular unit 601 in FIG. 38. The cross-section of the modular is unit 208 and is illustrated in FIG. 39 and the blowup representation of the same unit is illustrated in FIG. 40. Medically beneficial therapy delivering probe 618, is held by a stabilizer ring. This stabilizer ring 619, is pushed towards the patient anatomy 102 with the support of a spring (or an object with similar suspension qualities) 620. The mechanism comprises the therapy delivering probe (effector) and a stabilizer ring, and the spring is held together between the back lid 621 and the main body 601 of the modular unit. Arrow 622 illustrates the direction of contact with the patient anatomy. Sufficient contact between the therapy-delivering probe and the patient anatomy is crucial for delivering the therapeutic energy, and the spring acts as a buffer between the elements to accommodate edema development or other changes in the anatomy. A cable 623 connects the medically beneficial therapy delivering probe to a power source 624. Exemplary therapeutic applications delivered through probes and skin contact include LIPUS (low pulsed ultrasound stimulation), TENS (transcutaneous electrical nerve stimulation), EMS (electrical muscle stimulation), FES (functional electrical stimulation), NMERS (neuromuscular electrical stimulation), IFC (interferential current), High Voltage Stimulation, Iontophoresis etc.

In additional aspects, the present invention provides a method for fabricating a comfortable body interface as a hub for sensory technologies. In an embodiment structural dynamics of SMS is adapted to monitor circumferential changes in a cross-sectional portion.

Figure 41:
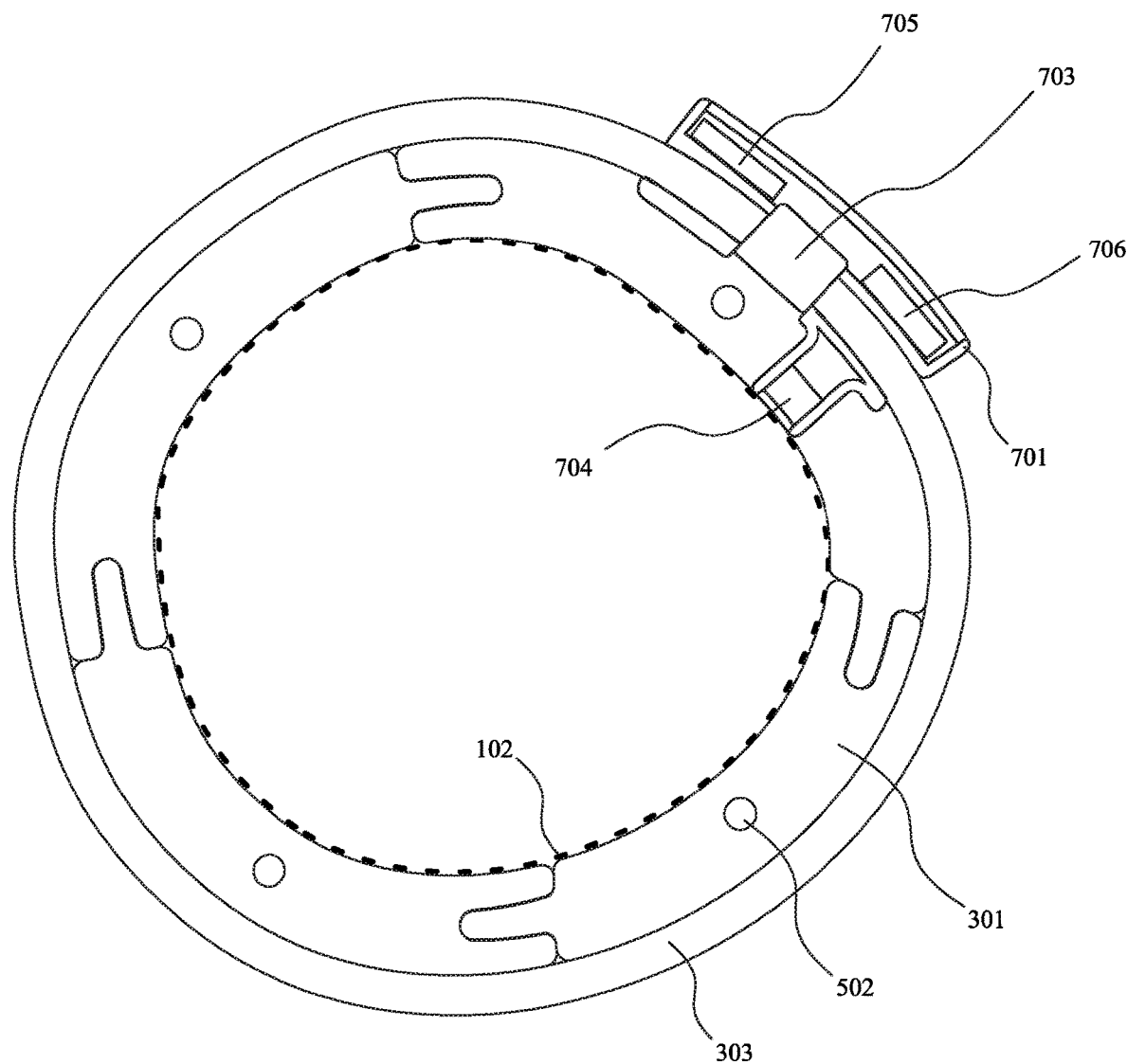
FIG. 41 is the cross-section of a circumferential sensor attached to a portion of a three-dimensional printed body scaffold with SMS.

A circumferential monitoring unit with a strain gauge, an electro conductive O-ring, a temperature sensor and relevant electronic components 701 is illustrated in FIG. 38. The cross-section 209 of the sensory unit is illustrated in FIG. 41. The adaptive orthotic structure is held to gather by pressure applied by the electrically conductive rubber O-ring 303. In the event of circumferential increase or decrease, the electrically conductive rubber O-ring will stretch or contract in response. A strain gauge sensor 702 can measure changes in electro-conductivity of the rubber O-ring due to stretching or contracting. Alternatively, the same system can be implemented to axial tethers. The sensory capabilities of the unit is also expanded with an additional temperature sensor 704, for monitoring the local body temperature of the patient, this data is also important since edema accumulation presents itself with an increased body temperature. The system also incorporates a microcomputer with relevant capabilities 705, batteries 706 or a receiver for wireless energy transfer system, and wiring. FIG. 42 is a cross-sectional view of the circumferential slip joint of splint of FIG. 29 illustrating the minimal tangential relationship between two circumferential portions. FIG. 43 is a cross-section of the circumferential slip joint of splint of FIG. 30 illustrating the sliding rail topology between two circumferential portions.

What is claimed is:

1. A method for fabricating a conformable body interface, said method comprising:

obtaining a data set representing a three-dimensional, soft tissue body surface; and fabricating a three-dimensional body scaffold which can be removably placed over the three-dimensional body surface to conform to at least some target regions of said surface;

wherein the data set defines a body scaffold which is divided into two or more longitudinal segments having axial joints therebetween and wherein said axial joints are configured to separate circumferentially in response to swelling of the body surface when the scaffold is placed over the body surface;

wherein the data set further defines two or more circumferentially split segments separated by circumferential joints which are configured to axially separate in response to movement of the body surface when the scaffold is placed over the body surface; and wherein the data set further defines axial channels on the body scaffold, which channels are configured to receive a plurality of axial tethers spanning the circumferential joints at circumferentially spaced-apart locations on the body scaffold to constrain bending of the body scaffold.

2. A method as in claim 1, wherein the data set further defines features on the body scaffold, which features are configured to receive a plurality of constraints spanning the axial joints at axially spaced-apart locations along the body scaffold to constrain radial expansion of the body scaffold in response to swelling of the body surface.

3. A method as in claim 2, further comprising attaching the constraints to the features spanning the axial joints and positioning axial tethers within the axial channels spanning the circumferential joints.

* * * * *